(12) United States Patent
Hammond et al.

(10) Patent No.: US 9,737,557 B2
(45) Date of Patent: Aug. 22, 2017

(54) NUCLEIC ACID PARTICLES, METHODS AND USE THEREOF

(71) Applicant: Massachusetts Institute of Technology, Cambridge, MA (US)

(72) Inventors: Paula T. Hammond, Newton, MA (US); Jong Bum Lee, Cambridge, MA (US); Young Hoon Roh, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 14/811,263

(22) Filed: Jul. 28, 2015

(65) Prior Publication Data

US 2016/0151404 A1    Jun. 2, 2016

Related U.S. Application Data

(63) Continuation of application No. 14/190,983, filed on Feb. 26, 2014, now abandoned.

(60) Provisional application No. 61/769,731, filed on Feb. 26, 2013.

(51) Int. Cl.
| | |
|---|---|
| *A61K 31/713* | (2006.01) |
| *C12N 15/113* | (2010.01) |
| *C12N 15/88* | (2006.01) |
| *A61K 9/16* | (2006.01) |
| *A61K 45/06* | (2006.01) |
| *C12P 19/34* | (2006.01) |
| *C12N 15/11* | (2006.01) |
| *A61K 9/50* | (2006.01) |
| *C12Q 1/68* | (2006.01) |

(52) U.S. Cl.
CPC ............ *A61K 31/713* (2013.01); *A61K 9/167* (2013.01); *A61K 9/50* (2013.01); *A61K 9/5089* (2013.01); *A61K 45/06* (2013.01); *C12N 15/111* (2013.01); *C12N 15/113* (2013.01); *C12N 15/88* (2013.01); *C12P 19/34* (2013.01); *C12N 2310/14* (2013.01); *C12N 2320/32* (2013.01); *C12Q 1/6844* (2013.01)

(58) Field of Classification Search
CPC ...... A61K 31/713; A61K 45/06; A61K 48/00; A61K 9/167; C12N 15/10; C12N 15/111; C12N 15/113; C12N 15/88; C12N 2310/14; C12N 2320/32; C12P 19/34
USPC ........................ 424/490; 435/91.2; 514/44 A
See application file for complete search history.

(56) References Cited

U.S. PATENT DOCUMENTS

| | | |
|---|---|---|
| 3,266,987 A | 8/1966 | Crowley et al. |
| 3,710,795 A | 1/1973 | Higuchi et al. |
| 3,962,414 A | 6/1976 | Michaels |
| 4,191,811 A | 3/1980 | Hodgdon |
| 4,250,029 A | 2/1981 | Kiser et al. |
| 4,460,563 A | 7/1984 | Calanchi |
| 4,638,045 A | 1/1987 | Kohn et al. |
| 4,794,000 A | 12/1988 | Ecanow |
| 4,806,621 A | 2/1989 | Kohn et al. |
| 4,946,929 A | 8/1990 | D'Amore et al. |
| 5,010,167 A | 4/1991 | Ron et al. |
| 5,019,379 A | 5/1991 | Domb et al. |
| 5,114,719 A | 5/1992 | Sabel et al. |
| 5,208,111 A | 5/1993 | Decher et al. |
| 5,364,634 A | 11/1994 | Lew |
| 5,399,665 A | 3/1995 | Barrera et al. |
| 5,462,990 A | 10/1995 | Hubbell et al. |
| 5,512,131 A | 4/1996 | Kumar et al. |
| 5,512,600 A | 4/1996 | Mikos et al. |
| 5,514,378 A | 5/1996 | Mikos et al. |
| 5,518,767 A | 5/1996 | Rubner et al. |
| 5,536,573 A | 7/1996 | Rubner et al. |
| 5,630,941 A | 5/1997 | Burger et al. |
| 5,660,873 A | 8/1997 | Nikolaychik et al. |
| 5,696,175 A | 12/1997 | Mikos et al. |
| 5,700,559 A | 12/1997 | Sheu et al. |
| 5,714,166 A | 2/1998 | Tomalia et al. |
| 5,716,404 A | 2/1998 | Vacanti et al. |
| 5,716,709 A | 2/1998 | Ferguson et al. |
| 5,736,372 A | 4/1998 | Vacanti et al. |
| 5,770,417 A | 6/1998 | Vacanti et al. |
| 5,797,898 A | 8/1998 | Santini, Jr. et al. |
| 5,804,178 A | 9/1998 | Vacanti et al. |
| 5,807,636 A | 9/1998 | Sheu et al. |

(Continued)

FOREIGN PATENT DOCUMENTS

| | | |
|---|---|---|
| DE | 19812083 A1 | 9/1999 |
| DE | 29907804 U1 | 10/1999 |

(Continued)

OTHER PUBLICATIONS

Grabow et al. Nature Materials, 11(4): 268-269. (2012).*

(Continued)

*Primary Examiner* — Janet Epps-Smith

(74) *Attorney, Agent, or Firm* — Foley Hoag LLP

(57) ABSTRACT

The present invention provides, among other things, a particle which includes a core comprised of self-assembled one or more nucleic acid molecules, the core being characterized by an ability to adopt at least two configurations: a first configuration having a first greatest dimension greater than 2 μm and; a second configuration having a second greatest dimension less than 500 nm, wherein addition of a film coating converts the core from its first configuration to its second configuration. Methods of making and using of provided particles are also disclosed.

51 Claims, 20 Drawing Sheets

(56) References Cited

U.S. PATENT DOCUMENTS

| | | |
|---|---|---|
| 5,837,377 A | 11/1998 | Sheu et al. |
| 5,837,752 A | 11/1998 | Shastri et al. |
| 5,858,746 A | 1/1999 | Hubbell et al. |
| 5,902,599 A | 5/1999 | Anseth et al. |
| 5,904,927 A | 5/1999 | Amiji |
| 5,962,520 A | 10/1999 | Smith et al. |
| 6,022,590 A | 2/2000 | Ferguson et al. |
| 6,060,582 A | 5/2000 | Hubbell et al. |
| 6,089,853 A | 7/2000 | Biebuyck et al. |
| 6,095,148 A | 8/2000 | Shastri et al. |
| 6,103,266 A | 8/2000 | Tapolsky et al. |
| 6,114,099 A | 9/2000 | Liu et al. |
| 6,123,681 A | 9/2000 | Brown, III |
| 6,123,727 A | 9/2000 | Vacanti et al. |
| 6,131,211 A | 10/2000 | Hennessey |
| 6,180,239 B1 | 1/2001 | Whitesides et al. |
| 6,235,224 B1 | 5/2001 | Mathiowitz et al. |
| 6,312,727 B1 | 11/2001 | Schacht et al. |
| 6,402,918 B1 | 6/2002 | Schlenoff et al. |
| 6,447,887 B1 | 9/2002 | Claus et al. |
| 6,451,871 B1 | 9/2002 | Winterton et al. |
| 6,479,146 B1 | 11/2002 | Caruso et al. |
| 6,492,096 B1 | 12/2002 | Liu et al. |
| 6,497,729 B1 | 12/2002 | Moussy et al. |
| 6,699,501 B1 | 3/2004 | Neu et al. |
| 6,716,813 B2 | 4/2004 | Lim et al. |
| 6,740,643 B2 | 5/2004 | Wolff et al. |
| 6,743,521 B2 | 6/2004 | Hubbell et al. |
| 6,833,192 B1 | 12/2004 | Caruso et al. |
| 6,860,980 B2 | 3/2005 | Locascio et al. |
| 6,896,926 B2 | 5/2005 | Qiu et al. |
| 6,919,373 B1 | 7/2005 | Lam et al. |
| 6,998,115 B2 | 2/2006 | Langer et al. |
| 7,045,087 B2 | 5/2006 | Kotov |
| 7,045,146 B2 | 5/2006 | Caruso et al. |
| 7,101,575 B2 | 9/2006 | Donath et al. |
| 7,101,947 B2 | 9/2006 | Schlenoff et al. |
| 7,112,361 B2 | 9/2006 | Lynn et al. |
| 7,223,327 B2 | 5/2007 | Schlenoff et al. |
| 7,303,814 B2 | 12/2007 | Lamberti et al. |
| 7,348,399 B2 | 3/2008 | Haynie |
| 7,364,585 B2 | 4/2008 | Weber |
| 7,365,142 B2 | 4/2008 | Schlenoff et al. |
| 7,427,354 B2 | 9/2008 | Eto |
| 7,427,394 B2 | 9/2008 | Anderson et al. |
| 7,491,263 B2 | 2/2009 | Wang et al. |
| 7,879,575 B2 | 2/2011 | Kricka et al. |
| 8,105,652 B2 | 1/2012 | Wood et al. |
| 2002/0053514 A1 | 5/2002 | Locascio et al. |
| 2002/0131933 A1 | 9/2002 | Delmotte |
| 2002/0131951 A1 | 9/2002 | Langer et al. |
| 2002/0187197 A1 | 12/2002 | Caruso et al. |
| 2003/0059398 A1 | 3/2003 | Ranger et al. |
| 2003/0113368 A1 | 6/2003 | Nomoto et al. |
| 2003/0124368 A1 | 7/2003 | Lynn et al. |
| 2004/0013721 A1 | 1/2004 | Antipov et al. |
| 2004/0020423 A1 | 2/2004 | Lewis et al. |
| 2004/0044100 A1 | 3/2004 | Schlenoff et al. |
| 2004/0052865 A1 | 3/2004 | Gower et al. |
| 2004/0149572 A1 | 8/2004 | Schlenoff et al. |
| 2005/0019404 A1 | 1/2005 | Sung et al. |
| 2005/0152955 A1 | 7/2005 | Akhave et al. |
| 2005/0208100 A1 | 9/2005 | Weber et al. |
| 2005/0276841 A1 | 12/2005 | Davis et al. |
| 2006/0127437 A1 | 6/2006 | Kennedy et al. |
| 2006/0198897 A1 | 9/2006 | Pacetti et al. |
| 2006/0216494 A1 | 9/2006 | Furedi-Milhofer et al. |
| 2006/0246112 A1 | 11/2006 | Snyder et al. |
| 2007/0020469 A1 | 1/2007 | Wood et al. |
| 2007/0077276 A1 | 4/2007 | Haynie |
| 2007/0083186 A1 | 4/2007 | Carter et al. |
| 2007/0129792 A1 | 6/2007 | Picart et al. |
| 2007/0141100 A1 | 6/2007 | Sung et al. |
| 2007/0197568 A1 | 8/2007 | Bunn et al. |
| 2007/0276330 A1 | 11/2007 | Beck et al. |
| 2008/0139450 A1 | 6/2008 | Madhyastha et al. |
| 2008/0228280 A1 | 9/2008 | Cohen et al. |
| 2008/0248108 A1 | 10/2008 | Krotz et al. |
| 2008/0311177 A1 | 12/2008 | Hammond et al. |
| 2009/0053139 A1 | 2/2009 | Shi et al. |
| 2009/0061006 A1 | 3/2009 | Leuschner et al. |
| 2009/0088479 A1 | 4/2009 | Allmendinger et al. |
| 2009/0088679 A1 | 4/2009 | Wood et al. |
| 2009/0155326 A1 | 6/2009 | Mack et al. |
| 2009/0170179 A1 | 7/2009 | Lynn et al. |
| 2009/0214615 A1 | 8/2009 | Zhao et al. |
| 2009/0246142 A1 | 10/2009 | Bhatia et al. |
| 2009/0258045 A1 | 10/2009 | Chuang et al. |
| 2009/0263468 A1 | 10/2009 | McAnulty et al. |
| 2009/0275906 A1 | 11/2009 | Berland et al. |
| 2010/0003499 A1 | 1/2010 | Krogman et al. |
| 2010/0016439 A1 | 1/2010 | Thomes et al. |
| 2010/0040674 A1 | 2/2010 | Smith et al. |
| 2010/0189683 A1 | 7/2010 | Holmlund et al. |
| 2011/0038939 A1 | 2/2011 | Lvov et al. |
| 2011/0114244 A1 | 5/2011 | Yoo et al. |
| 2011/0143127 A1 | 6/2011 | Gupta et al. |
| 2011/0301209 A1 | 12/2011 | Zaknoen et al. |
| 2012/0027837 A1 | 2/2012 | DeMuth et al. |
| 2012/0058355 A1 | 3/2012 | Lee et al. |
| 2012/0277719 A1 | 11/2012 | Shukla et al. |
| 2012/0277852 A1 | 11/2012 | Shukla et al. |
| 2013/0190890 A1 | 7/2013 | Shah et al. |
| 2013/0273137 A1 | 10/2013 | Mandell et al. |
| 2014/0011759 A1 | 1/2014 | Yaffe et al. |
| 2014/0039575 A1 | 2/2014 | Bradley |
| 2014/0302116 A1 | 10/2014 | Castleberry et al. |

FOREIGN PATENT DOCUMENTS

| | | |
|---|---|---|
| EP | 0 443 809 A2 | 8/1991 |
| EP | 1 116 516 A1 | 7/2001 |
| EP | 2 162 283 A2 | 3/2010 |
| EP | 2 566 468 A2 | 3/2013 |
| EP | 2 701 908 A1 | 3/2014 |
| GB | 1213803 A | 11/1970 |
| GB | 1213805 A | 11/1970 |
| WO | WO-95/11748 A1 | 5/1995 |
| WO | WO-95/34595 A1 | 12/1995 |
| WO | WO-96/03147 A1 | 2/1996 |
| WO | WO-98/03573 A1 | 1/1998 |
| WO | WO-98/17330 A1 | 4/1998 |
| WO | WO-98/47948 A1 | 10/1998 |
| WO | WO-99/47253 A1 | 9/1999 |
| WO | WO-99/59647 A1 | 11/1999 |
| WO | WO-00/77281 | 12/2000 |
| WO | WO-01/57118 | 8/2001 |
| WO | WO-01/94441 | 12/2001 |
| WO | WO-02/085500 | 10/2002 |
| WO | WO-03/035716 | 5/2003 |
| WO | WO-2006/051227 A1 | 5/2006 |
| WO | WO-2006/086391 A2 | 8/2006 |
| WO | WO-2007/140391 A2 | 12/2007 |
| WO | WO-2007/140402 A1 | 12/2007 |
| WO | WO-2008/157372 A2 | 12/2008 |
| WO | WO-/2010/021973 A2 | 2/2010 |
| WO | WO-2010/120531 A2 | 10/2010 |
| WO | WO-2011/140136 A1 | 11/2011 |
| WO | WO-2012/149492 A1 | 11/2012 |
| WO | WO-2012/149494 A2 | 11/2012 |
| WO | WO-2013/110047 A1 | 7/2013 |
| WO | WO-2013/163234 A1 | 10/2013 |
| WO | WO-2014/059269 A2 | 4/2014 |
| WO | WO-2014/066862 A2 | 5/2014 |
| WO | WO-2014/150074 A1 | 9/2014 |

OTHER PUBLICATIONS

Lee et al. Nature Materials, 11(4):316-322 (2012).*
Abeloff, M.D. et al., Chapter 95: Cancer of the Breast, in Abeloff's Clinical Oncology, Fourth Edition, pp. 1875-1943, Churchill Livingstone Elsevier (2008).

(56) References Cited

OTHER PUBLICATIONS

Abramoff et al., "Image Processing with ImageJ" Biophotonics International 2004, 11, 36-42.
Absolom et al., "Protein adsorption to polymer particles: role of surface properties" *J Biomed Mater Res.* Feb. 1987;21(2):161-71.
Afonin, K. A. et al. In vitro assembly of cubic RNA-based scaffolds designed in silico. Nature Nanotechnol. 5, 676-682 (2010).
Ai et al., Biomedical applications of electrostatic layer-by-layer nano-assembly of polymers, enzymes, and nanoparticles' *Cell Biochem Biophys.* 2003;39(1):23-43.
Akinc et al., "Synthesis of poly(beta-amino ester)s optimized for highly effective gene delivery" *Bioconjugate Chem.* 2003, 14:979-988.
Akinc, A. et al. A combinatorial library of lipid-like materials for delivery of RNAi therapeutics. Nature Biotechnol. 26, 561-569 (2008).
Albeck, J.G. et al., Modeling a Snap-Action, Variable-Delay Switch Controlling Extrinsic Cell Death, *PLoS Biology*, 6(12):2831-2852 (2008).
Albrektsson et al., "Osteoinduction, osteoconduction and osseointegration" *Eur Spine J.* Oct. 2001;10 Suppl 2:S96-101.
Alsberg E, Hill EE, Mooney DJ. Craniofacial tissue engineering. Critical reviews in oral biology and medicine : an official publication of the American Association of Oral Biologists 2001, 12(1): 64-75.
Alsberg E, Kong HJ, Hirano Y, Smith MK, Albeiruti A, Mooney DJ. Regulating bone formation via controlled scaffold degradation. J Dent Res 2003, 82(11): 903-908.
Alvarez-Roman, R., Naik, A., Kalia ,Y. N., Guy, R. H. & Fessi ,H. Skin penetration and distribution of polymeric nanoparticles. J. Controlled ReJease 99 ,53-62,doi:10.1016/j.jconrel.2004.06.015 (2004).
Alves et al., "Self assembling and crosslinking of polyelectrolyte multilayer films of chitosan and alginate studied by QCM and IR spectroscopy" *Macromol Biosci.* Aug. 11, 2009;9(8):77685.
Anderson et al., "Semi-Automated Synthesis and Screening of a Large Library of Degradable Cationic Polymers for Gene Delivery," Angew. Chem. Int. Ed. 42:3151-3158 (2003).
Anderson, "Human Gene Therapy" *Nature*, 392: 25-30 (1996).
Anderson, et al., "Biodegradation and Biocompatibility of PLA and PLGA Microspheres" *Adv. Drug Delivery Rev.* 28: 5-24, 1997.
Ando, et al., "PLGA Micospheres Containing Plasmid DNA: Preservation of Supercoiled DNA via Cryopreparation and Carbohydrate Stabilization" *J. Pharm. Sci.* 88: 126-130, 1999.
Antipov, et al., "Sustained Release Properties of Polyelectrolyte Multilayer Capsules" *J. Phys. Chem.*, 105:2281-2284 (2001).
Ariga et al., "Layer-by-layer assembly as a versatile bottom-up nanofabrication technique for exploratory research and realistic application" *Phys Chem Chem Phys.* May 21, 2007;9(19):2319-40.
Balabushevich et al., "Protein-loaded microspheres prepared by sequential adsorption of dextran sulphate and protamine on melamine formaldehyde core" *J Microencapsul.* Nov. 2009;26(7):571-9.
Balko, J.M. et al., Gene expression patterns that predict sensitivity to epidermal growth factor receptor tyrosine kinase inhibitors in lung cancer cell lines and human lung tumors, *BMC Genomics*, 7:289-302 (2006).
Barrera et al., "Synthesis and RGD peptide modification of a new biodegradable copolymer: poly(lactic acid-co-lysine)" *J. Am. Chem. Soc.* 115:11010-11011, 1993.
Bass, Brenda L., "RNA Interference the Short Answer", Nature 411, 428-429, 2001.
Behr, "Synthetic Gene-Transfer Vectors" *Ace. Chem. Res.* 26: 274-278, 1993.
Behr, "The Proton Sponge: a Trick to Enter Cells the Viruses Did Not Expoit" *Chimia*, 51: 34-36, 1997.
Benkirane-Jessel et al., "Build-up if Polypeptide Multilayer Coatings with Anti-Inflammatory Properties Based on the Embedding of Piroxicam-Cyclodextrin Complexes," *Advanced Functional Materials.* 14:2, 2004.
Berg et al., "Controlling mammalian cell interactions on patterned polyelectrolyte multilayer surfaces" *Langmuir.* Feb. 17, 2004;20(4)1 362-8.
Bershteyn et al., "Polymer-supported lipid shells, onions, and flowers" *Soft Matter* 2008, 4, 1787.
Beyer, S., Nickels, P. & Simmel, F.C. Periodic DNA nanotemplates synthesized by rolling circle amplification, Nano Lett 5, 719-722 (2005).
Biggs et al., "The use of nanoscale topography to modulate the dynamics of adhesion formation in primary osteoblasts and ERK/MAPK signalling in STRO-1+ enriched skeletal stem cells" *Biomaterials* Oct. 2009;30(28):5094-103.
Bins,A. D. et al. A rapid and potent DNA vaccination strategy defined by in vivo monitoring of antigen expression. Nat. Med. (N. Y.,NY,U.5.) 11,899-904,doi:10.1038/nm1264 (2005).
Blacklock et al., "Cross-linked bioreducible layer-by-layer films for increased cell adhesion and transgene expression" *J Phys Chem B.* Apr. 29;114(16):5283-91.
Boes et al., "T-cell engagement of dendritic cells rapidly rearranges MHC class II transport" Nature 2002, 418, 983-988.
Bonewald et al., "von Kossa staining alone is not sufficient to confirm that mineralization in vitro represents bone formation" *Calcif Tissue Int.* May 2003;72(5):537-47.
Bott "Applications of "Wired" Enzyme Electrodes," *Current Separations*, 21(1):3-6 (2004).
Boudou et al., "Internal composition versus the mechanical properties of polyelectrolyte multilayer films: the influence of chemical cross-linking" *Langmuir.* Dec. 15, 2009;25(24):13809-19.
Boudou et al., "Multiple functionalities of polyelectrolyte multilayer films: new biomedical applications" *Adv. Mater.*, 22(4):441-467 (2010).
Boussif, et al., "A Versatile Vector for Gene and Oligonucleotide Transfer into Cells in Culture and in Vivo: Polyethylenimine" *Proc. Nat/. Acad. Sci, USA*, 92: 7297-7301, 1995.
Brama et al., "Effect of titanium carbide coating on the osseointegration response in vitro and in vivo" *Biomaterials.* Feb. 2007;28(4):595-608.
Brange et al., "Insulin formulation and delivery" *Pharm Biotechnol.* 1997;10:343-409.
Brazeau, et al., "In Vitro Myotoxicity of Selected Cationic Macromolecules Used in Non-ltbl Gene Delivery" *Pharm. Res.* 15: 680-684, 1998.
Brewer et al., "Condensation Of Dna by spermatid basic nuclear proteins" *J Biol Chem.* Oct. 11, 2002;277(41):38895-900.
Brewster et al. 2007, "Cyclodextrins as Pharmaceutical Solubilizers," *Advanced Drug Delivery.* 59: 645-666).
Buser et al., "The Crystal Structure of Prussian Blue: Fe4[Fe(CN)5]3XH20," *Inorganic D Chemistry*, 16(11 ):2704-271 0 (1977).
Calvo et al. "Donnan Permselectivity in Layer-by-Layer Self-Assembled Redox Polyelectrolyte thin film", *J. AM. SOC.* 124: 8490-8497 (2002).
Carey, L.A. et al., "EGFR inhibition with cetuximab added to carboplatin in metastatic triple-negative (basal-like) breast cancer," Supplement to Journal of Clinical Oncology, ASCO Annual Meeting Proceedings, TBCRC 001: Clinical Science Symposium, 43S (2009).
Carpenter et al., "A Single-Film Electrochromic Device," *J. Electrochem. Soc.*, 137(8):2464-2467 (1990).
Carpenter, A. E. et al., CellProfiler: image analysis software for identifying and quantifying cell phenotypes, *Genome Biology*, 7(10):R100-R100.11 (2006).
Carragee EJ, Hurwitz EL, Weiner BK. A critical review of recombinant human bone morphogenetic protein-2 trials in spinal surgery: emerging safety concerns and lessons learned. Spine J 2011, 11(6): 471-491.
Carrell et al., "The aetiology of sperm protamine abnormalities and their potential impact on the sperm epigenome" *Int J Androl.* Dec. 2008;31(6):537-45.
Castleberry, S., et al., "Nanolayered siRNA Dressing for Sustained Localized Knockdown," ACS NANO, 7(6): 5251-5261 (2013).

(56) References Cited

OTHER PUBLICATIONS

Castleberry, S., et al., "Surface Mediated Delivery of siRNA from Layer-By-Layer Assembled Polyelectrolyte Films for the Acceleration of Wound Healing," Abstracts of Papers, 244th National Mtg & Exposition, Aug. 19-23 (2012).
Cavalieri et al., "Assembly and functionalization of DNA-polymer microcapsules" ACS Nano 2009, 3, 234.
Chen, "Preparation, characterization, and electrocatalytic oxidation properties of iron, cobalt, nickel, and indium hexacyanoferrate," Journal of Electroanalytical Chemistry, 521:29-52 (2002).
Choksakulnimitr et al., "In Vitro Cytotoxicity of Macromolecules in Different Cell Culture Systems" Controlled Release, 34: 233-241 (1995).
Chou, T-C. et al., Quantitative Analysis of Dose-Effect Relationships: The Combined Effects of Multiple Drugs or Enzyme Inhibitors, Advances in Enzyme Regulation, 22:27-55 (1984).
Christensen et al., "Heparin coating of the stent graft—effects on platelets, coagulation and complement activation," Biomaterials, 22:349-355 (2001).
Cini et al., "Step-by-step assembly of self-patterning polyelectrolyte films violating (almost) all rules of layer-by-layer deposition" J Am Chem Soc. Jun. 23;132(24):8264-5.
Clark et al., "Selective Deposition in Multilayer Assembly: SAMs as molecular templates," Supramolecular Science 4:141, 1997.
Corkery, B. et al., Epidermal growth factor receptor as a potential therapeutic target in triple-negative breast cancer, Annals of Oncology, 20:862-867 (2009).
Cotten, et al., "Receptor-Mediated Transport of DNA into Eukaryotic Cells" Methods Enzym. 217:618, 1993.
Crane et al., "Cyclodextrin Inclusion Complexes with a Solvatochromic Fluorescent Probe," Journal of Chemical Education. 79(10):1261-1263 (2002).
Crouzier et al., "Ion pairing and hydration in polyelectrolyte multilayer films containing polysaccharides" Biomacromolecules. Feb. 9, 2009;10(2):433-42.
Crouzier T, Sailhan F, Becquart P, Guillot R, Logeart-Avramoglou D, Picart C. The performance of BMP-2 loaded TCP/HAP porous ceramics with a polyelectrolyte multilayer film coating. Biomaterials 2011, 32(30): 7543-7554.
Crystal, "Transfer of Genes to Humans: Early Lessons and Obstacles to Success" Science, 270: 404-410 (1995).
Dalby et al., "The control of human mesenchymal cell differentiation using nanoscale symmetry and disorder" Nat Mater. Dec. 2007;6(12):997-1003.
Danhier F, Ansorena E, Silva JM, Coco R, Le Breton A, Preat V. PLGA-based nanoparticles: an overview of biomedical applications. J Control Release 2012, 161(2): 505-522.
Danusso, et al., "Synthesis of Tertiary Amine Polymers" Polymer, 11:88-113 (1970).
Daubendiek, S. L., Ryan, K. & Kool, E. T. Rolling-circle RNA-synthesis—circular oligonucleotides as efficient substrates for T7 RNA-polymerase. J. Am. Chem. Soc. 117, 7818-7819 (1995).
Davis et al., "Challenges and potential for RNA nanoparticles (RNPs)" J Biomed Nanotechnol, 5(1):36-44 (2009).
Davis et al., "Cyclodextrin-Based Pharmaceutics: Past, Present and Future," Nature Reviews (3), 1023-1035 (2004).
Davis, M. E. et al. Evidence of RNAi in humans from systemically administered siRNA via targeted nanoparticles. Nature 464, 1067-1070 (2010).
de Jonge et al., "The osteogenic effect of electrosprayed nanoscale collagen/calcium phosphate coatings on titanium" Biomaterials. Mar;31(9):2461-9.
Decher et al., "Layer-by-layer assembled multicomposite films," Curr. Opinion Coli. & Interf. Sci. 3:32-39 (1998).
Decher et al., "New nanocomposite films for biosensors: layer-by-layer adsorbed films of polyelectrolytes, proteins or DNA," Biosensors & Bioelectronics, 9:677-684 (1994).
Decher et al., "Buildup of Ultrathin Multilayer Films by a Self-Assembly Process, 1 Consecutive Adsorption of Anionic and Cationic Bipolar Amphiphiles on Charged Surfaces," Makromol. Chem., Macro mol. Symp., 46:321-327 (1991).
Decher, "Fuzzy Nanoassemblies: Toward Layered Polymeric Multicomposites" Science, 277: 1232-1237 (1997).
Decher, et al., "Buildup of Ultrathin Multilayer Films by a Self-Assembly Process: II. Consecutive Adsorption of Anionic and Cationic Bipolar Amphiphiles and Polyelectrolytes on Charged Surfaces," Ber. Bunsenges. Phys. Chem., 95(11)1430-1434 (1991).
Delongchamp "High-Contrast Electrochromism from Layer-By-Layer Polymer Films," Chem. Mater, 15: 1575-1586 (2003).
Delongchamp et al., "Fast Ion Conduction in Layer-By-Layer Polymer Films," Chem. Mater., 15:1165-1173 (2003).
Delongchamp et al., "High-Contrast Electrochromism and Controllable Dissolution of Assembled Prussian Blue/Polymer Nanocomposites,""Adv. Funct. Mater., 14(3):224-231 (2004).".
Demeneix, et al., "The Proton Sponge: A Trick the Viruses Did Not Exploit," American Chemical Society,146-151 (1996).
DeMuth et al., "Nano-layered microneedles for transcutaneous delivery of polymer nanoparticles and plasmid DNA" Adv Mater. Nov 16;22(43):4851-6.
DeMuth PC, Min YJ, Huang B, Kramer JA, Miller AD, Barouch DH, et al. Polymer multilayer tattooing for enhanced DNA vaccination. Nature Materials 2013, 12(4): 367-376.
Dent, R. et al., "Triple-Negative Breast Cancer: Clinical Features and Patterns of Recurrence," Clinical Cancer Research, 13: 4429-4434 (2007).
Deshmukh, et al., "Liposome and Polylysine Mediated Gene Transfer" New J. Chem. 21: 113-124 (1997).
Diaz, R. et al., "Antitumor and anti angiogenic effect of the dual EGFR and HER-2 tyrosine kinase inhibitor lapatinib in a lung cancer model," BMC Cancer, 10:188 (2010).
Diegelman, A. M. & Kool, E. T. Generation of circular RNAs and trans-cleaving catalytic RNAs by rolling transcription of circular DNA oligonucleotides encoding hairpin ribozymes. Nucleic Acids Res. 26, 3235-3241 (1998).
Dimitriou R, Jones E, McGonagle D, Giannoudis PV. Bone regeneration: current concepts and future directions. BMC medicine 2011, 9: 66.
Dimitrova et al., "Sustained delivery of siRNAs targeting viral infection by cell-degradable multilayered polyelectrolyte films" Proc. Natl. Acad. Sci. U. S. A. 2008, 105, 16320.
Dixon, "Quartz crystal microbalance with dissipation monitoring: enabling real-time characterization of biological materials and their interactions" J Biomol Tech. Jul. 2008;19(3):151-8.
Doh, J. & Irvine ,D. J. Photogenerated polyelectrolyte bilayers from an aqueous-processible photoresist for multicomponent protein patterning. J. Am. Chem. Soc. 126, 9110-9171 (2004).
Doh, J. & Irvine, D. J. Aqueous-processible photoresist polymer for multiple protein patterning: Synthesis, characterization and application to T cell activation. PMSE Prepr. 93, 327-328 (2005).
Dowben, R.M., "General Physiology: A Molecular Approach," Division of Biological and Medical Sciences, pp. 142-143, Harper & Row Publishers (1969).
Dubas, et al., "Multiple Membranes from 'True' Polyelectrolyte Multilayers", J. Am. Chem. Soc., 123:5368-5369 (2001).
Dubas, et al., Polyelectrolyte Multilayers Containing a Weak Polyacid: Construction and Deconstruction, Macromolecules, 34: 3736-3740 (2001).
Duek et al., "A Solid-State Electrochromic Device Based on Polyaniline, Prussian Blue and an Elastomeric Electrolyte," Advanced Materials, 5(9):650-652 (1993).
Ekins, S. et al., Pathway Mapping Tools for Analysis of High Content Data, Methods in Molecular Biology, 356:319-350 (2007).
Ekwueme, Donatus et al., "Model-based estimates of risks of disease transmission and economic costs of seven injection devices in sub-Saharan Africa" Bull World Health Organ 2002, 80, 859-870.
El-Ghannam et al., "Model surfaces engineered with nanoscale roughness and RGD tripeptides promote osteoblast activity" J Biomed Mater Res A. Mar. 15, 2004;68(4):615-27.
Elbakry, A. et al. Layer-by-layer assembled gold nanoparticles for siRNA delivery. Nano Lett. 9, 2059-2064 (2009).

(56) References Cited

OTHER PUBLICATIONS

Elbashir, S.M. et al. Duplexes of 21-nucleoties RNAs mediate RNA interference in cultured mammalian cells. Nature 411, 494-498 (2011).
Elbert et al., "Self-assembly and steric stabilization at heterogeneous, biological surfaces using absorbing block copolymers" Chemistry & Biology 5(3): 177-183 (1998).
Ellis et al., "Eietrochromism in the Mixed-Valence Hexacyanides. 1. Voltammetric and Spectral Studies of the Oxidation and Reduction of Thin Films of Prussian Blue," J. Phys. Chem., 85:1225-1231 (1981).
European Search Report of 08771046.3, entitled "Self Assembled Films for Protein and Drug Delivery Applications," dated Oct. 22, 2012, 4 pages.
Facca S, Cortez C, Mendoza-Palomares C, Messadeq N, Dierich A, Johnston AP, et al. Active multilayered capsules for in vivo bone formation. Proc Natl Acad Sci U S A 2010, 107(8): 3406-3411.
Feiler et al., "Adsorption and viscoelastic properties of fractionated mucin (BSM) and bovine serum albumin (BSA) studied with quartz crystal microbalance (QCM-D)" J Colloid Interface Sci. Nov. 15, 2007;315(2):475-81.
Ferruti, e.t al., "Synthesis, Characterisation and Anti tumour Activity of Platinum (II) Complexes of Novel Functionalised Poly (Arnido Amine)s" Macromol. Chem. Phys., 200:1644-1654 (1999).
Ferruti, et al., "Amphoteric Linear Poly(amido-amine)s as Endosomolytic Polymers": Correlation between Physicochemical and Biological Properties", Macromolecules, 2000.
Ferruti, et al., "Linear Amino Polymers: Synthesis, Protonation and Complex Formation" Advances in Polymer Science, 58: 55-92, 1984.
Ferruti, et al., "Recent Results on Functional Polymers and Macromonomers offuterest as Biomaterials or for Biomaterial Modifcation" Biomaterials, 15: 1235-1241 (1994).
Ferruti, et al., "Synthesis, Physico-Chemical Properties and Biomedical Applications of Poly(amino-amine)s" Polymer, 26: 1336 (1985).
Fire, et al., "Potent and Specific Genetic Interference by Double-Stranded RNA in Caenorhabditis Elegans" Nature, 391: 806-811 (1998).
Fitzgerald, J.B. et al., Systems biology and combination therapy in the quest for clinical efficacy,Nature Chemical Biology, 2(9):458-466 (2006).
Flessner, R.M., et al., "Degradable Polyelectrolyte Multilayers That Promote the Release of siRNA," Langmuir, 27(12): 7868-7876 (2011).
Freiberg et al., "Polymer microspheres for controlled drug release," Int. J. Pharm. 282:1-18 (2004).
Friedman, "Human Gene Therapy—An Immature Genie, But Certainly out of the Bottle" Nature Med, 2: 144-147 (1996).
Gao et al., "Layer-by-layer electrodeposition of redox polymers and enzymes on screenprinted carbon electrodes for the preparation of reagentless biosensors," ChemComm, (2003).
Gaudet, S. et al., A Compendium of Signals and Responses Triggered by Pro-death and Prosurvival Cytokines, Molecular & Cellular Proteomics, 4:1569-1590 (2005).
Gemici et al., "Hydrothermal treatment of nanoparticle thin films for enhanced mechanical durability" Langmuir. Mar. 4, 2008;24(5):2168-77.
Gerasimov, et al., "Cytosolic Drug Delivery Using pH- and Light—Sensitive Liposomes" Adv. Drug Delivery Rev. 38: 317-338, 1999.
Giljohann, D. A., Seferos, D. S., Prigodich, A. E., Patel, P. C. & Mirkin, C. A. Gene regulation with polyvalent siRNA-nanoparticle conjugates. J. Am. Chem. Soc. 131, 2072-2073 (2009).
Gill et al., "Coated microneedles for transdermal delivery" J. Controlled Release 2007, 117, 227-237.
Gill et al., "Cutaneous vaccination using microneedles coated with hepatitis C DNA vaccine" Gene Ther. 2010.
Giudice et al., "Needle-free vaccine delivery" Adv. Drug Delivery Rev. 2006, 58, 68.
Glenn et al., "Transcutaneous immunization and immunostimulant strategies: capitalizing on the immunocompetence of the skin" Expert Rev. Vaccines, 2: 253 (2003).
Gonzalez, et al., "New Class of Polymers for the Delivery of Macromolecular Therapeutics" Bioconjugate Chem. 10: 1068-1074, 1999.
Grabow, W. W., et al., "siRNA delivery: Loaded-up Microsponges," Nature Materials, 11(4): 268-269 (2012).
Grabowski G, Cornett CA. Bone graft and bone graft substitutes in spine surgery: current concepts and controversies. The Journal of the American Academy of Orthopaedic Surgeons 2013, 21(1): 51-60.
Graham P.D., et al., "Phase inversion dynamics of PLGA solutions related to drug delivery," J Control Release 58(2): 233-245 (1999).
Grayson et al., "Electronic MEMS for triggered drug delivery," Advanced Drug Delivery Reviews, 56:173-184 (2004).
Greenland et al., "Beta-amino ester polymers facilitate in vivo DNA transfection and adjuvant plasmid DNA immunization" Mol. Ther. 2005, 12, 164.
Grewal, S. I. & Moazed, D. Heterochromatin and epigenetic control of gene expression. Science 301, 798-802 (2003).
Guo, P. RNA nanotechnology: Engineering, assembly and applications in detection, gene delivery and therapy. J. Nanosci. Nanotechnol. 5, 1964-1982 (2005).
Guo, P. The emerging field of RNA nanotechnology. Nature Nanotechnol. 5, 833-842 (2010).
Guo, P., "Rolling Circle Transcription of Tandem siRNA to Generate Spherulitic RNA Nanoparticles for Cell Entry," Molecular Therapy, Nucleic Acids, 1:3162-2531 (2012).
Habib et al., "A tungsten-trioxide/prussian blue complementary eletrochromic cell with a polymer electrolyte," Journal of Applied Electrochemistry, 21:203-207 (1991).
Habib et al., "Effect of Temperature on a Complementary W03-Prussian Blue Electrochromic System," J. Electrochem. Soc., 139(8):2155-2157 (1992).
Haensler, et al., "Polyamidoamine Cascade Polymers Mediate Efficient Transfection of Cells in Culture" Bioconjugate Chem. 4:372-379, 1993.
Hammond et al., "Formation of Polymer Microstructures by Selective Deposition of Polyion Multilayers Using Patterned Self-Assembled Monolayers as a Template," Macromolecules 28:7569-7571 (1995).
Hammond, "Form and Function in Multilayer Assembly: New Applications at the Nanoscale," Adv. Mater. 16:1271-1293 (2004).
Hanahan, D. et al., The Hallmarks of Cancer, Cell, 100 57-70 (2000).
Hanes, et al., "New Advances in Microsphere-Based Single-Dose Vaccines" Adv. Drug Delivery Rev. 28:97-119,1997.
Hansen, et al., "Re-Examination and Further Development of a Precise and Rapid Dye Method for Measuring Cell Growth/Cell Kill" Immunol. Methods, 119:203-210, 1989.
Haq et al., "Clinical administration of microneedles: Skin puncture, pain and sensation" Biomed Microdevices 2009, 11, 35.
Harper, J.W. et al., The DNA Damage Response: Ten Years After, Molecular Cell, 28(5):739-745 (2007).
Haynie et al., "Protein-inspired multilayer nanofilms: science, technology and medicine" Nanomedicine. Sep. 2006;2(3):150-7.
Hehrlein et al., "Drug-eluting stent: the "magic bullet" for prevention of restenosis?" Basic Res Cardiel, 97:417-423 (200:2).
Helfrich, B.A. et al., Antitumor Activity of the Epidermal Growth Factor Receptor (EGFR) Tyrosine Kinase Inhibitor Gefitinib (ZD1839, Iressa) in Non-Small Cell Lung Cancer Cell Lines Correlates with Gene Copy Number and EGFR Mutations but not EGFR Protein Levels, Clinical Cancer Research, 12:7117-7125 (2006).
Heller "Redox hydrogel-based electrochemical biosensore," Biosensors, Second Edition, pp. 1-18 (2004).
Hendrix, R. W. Bacteriophage DNA packaging: RNA gears in a DNA transport machine. Cell 94, 147-150 (1998).
Hill, et al., "In Vitro Cytotoxicity of Poly(amidoamine)s: Relevance to DNA Delivery" Biochim. Biophys. Acta, 1427: 16Iq 74, 1999.

(56) References Cited

OTHER PUBLICATIONS

Hillberg et al., "Effect of genipin cross-linking on the cellular adhesion properties of layer-bylayer assembled polyelectrolyte films" Biomaterials Sep. 2009;30(27):4463-70.
Hope, et al., Cationic Lipids, Phosphatidylethanolamine and the Intracellular Delivery of Polymeric, Nucleic Acid-Based Drugs (Review), Molecular Membrane Technology, 15: 1-14, 1998.
Hossfeld, S., et al., "Bioactive Coronary Stent Coating Based on Layer-By-Layer Technology for SiRNA release," Acta Biomaterialia, 9(5): 6741-6752 (2013).
International Preliminary Examination Report for PCT/US2002/34191, entitled: Methods of Making Decomposable Thin Films of Polyelectrolytes and Uses Thereof, Date of completion of report: Sep. 11, 2003.
International Preliminary Report on Patentability and Written Opinion for PCT/US2009/054011, entitled: Controlled Delivery of Bioactive Agents From Decomposable Films: Date of issuance: Feb. 22, 2011.
International Preliminary Report on Patentability and Written Opinion for PCT/US2012/035689, entitled: Coating Compositions, Methods and Coated Devices, Date of Issuance: Oct. 29, 2013.
International Preliminary Report on Patentability for PCT/US08/66948, entitled: Self Assembled Films for Protein and Drug Delivery Applications: Date of Issuance: Dec. 17, 2009.
International Preliminary Report on Patentability for PCT/US2006/004295, entitled: Electrochemically Degradable Layer-By-Layer Thin Films, Date of Issuance: Aug. 7, 2007.
International Preliminary Report on Patentability for PCT/US2007/069937, entitled: Methods of Making Decomposable Thin Films of Polyelectrolytes and Uses Thereof, Date of Issuance: Dec. 3, 2008.
International Preliminary Report on Patentability for PCT/US2007/69964, entitled: Methods of Making Decomposable Thin Films of Polyelectrolytes and Uses Thereof, Date of Issuance: Dec. 3, 2008.
International Preliminary Report on Patentability for PCT/US2011/035057, entitled: Drug Deliver Coating and Devices, Date of issuance: Nov. 6, 2012.
International Preliminary Report on Patentability for PCT/US2012/035692, entitled: Coating Compositions, Methods and Coated Devices, Date of Issuance: Oct. 29, 2013.
International Preliminary Report on patentability for PCT/US2013/022430, entitled: Compositions and Methods for Coating, Date of mailing: Jul. 22, 2014.
International Preliminary Report on Patentability for PCT/US2013/037868, entitled: Compositions and Methods of Treatment of Drug Resistant Cancers, Date of Mailing: Nov. 20, 2014.
International Preliminary Report on Patentability for PCT/US2013/37869, entitled: Stable Layer-By-Layer Coated Particles, Date of Mailing: Nov. 6, 2014.
International Search Report and Written Opinion for PCT/US2007/69964, entitled: Methods of Making Decomposable Thin Films of Polyelectrolytes and Uses Thereof, Date of Issuance: Oct. 29, 2007.
International Search Report for PCT/US08/66948: entitled: Self Assembled Films for Protein and Drug Delivery Applications: Date of Mailing: Aug. 29, 2008. (incorrectly cited as Aug. 23, 2008).
International Search Report for PCT/US2002/34191, entitled: Methods of Making Decomposable Thin Films of Polyelectrolytes and Uses Thereof, Date mailed: Jan. 17, 2003.
International Search Report for PCT/US2006/004295, entitled: Electrochemically Degradable Layer-By-Layer Thin Films, Date of Issuance: Oct. 2, 2006.
International Search Report for PCT/US2007/069937, entitled: Methods of Making Decomposable Thin Films of Polyelectrolytes and Uses Thereof, Date of mailing: Aug. 13, 2008.
International Search Report for PCT/US2009/054011, entitled: Controlled Delivery of Bioactive Agents From Decomposable Films: Date of mailing: Nov. 24, 2010.
International Search Report for PCT/US2011/035057, entitled: Drug Deliver Coating and Devices, Date of mailing: Feb. 8, 2012.
International Search Report for PCT/US2012/035689, entitled: Coating Compositions, Methods and Coated Devices, Date of Mailing: Jul. 31, 2012.
International Search Report for PCT/US2012/35692, entitled: Coating Compositions, Methods and Coated Devices, Date of Mailing: Oct. 5, 2012.
International Search Report for PCT/US2013/022430, entitled: Compositions and Methods for Coating, Date of mailing: May 15, 2013.
International Search Report for PCT/US2013/066980, entitled: Devices and Methods for Layer-by-Layer Assembly, Date of Mailing: Apr. 30, 2014.
International Search Report for PCT/US2013/37868, entitled: Compositions and Methods of Treatment of Drug Resistant Cancers, Date of Mailing: Sep. 6, 2013.
International Search Report for PCT/US2013/37869, entitled: Stable Layer-By-Layer Coated Particles, Date of Mailing: Sep. 13, 2013.
International Search Report for PCT/US2014/018284, entitled:Nucleic Acid Particles, Methods and Use Thereof, Date of mailing: Jul. 30, 2014.
International Search Report for PCT/US2014/022107, entitled: Compositions and Methods for Nucleic Acid Delivery, Date of mailing: Jun. 5, 2014.
Itaya et al., "Prussian-blue-modified electrodes: An application for a stable eletrochromic display device," J. Appl. Phys., 53:804-805 (1982).
Janes, K.A. et al., A Systems Model of Signaling Identifies a Molecular Basis Set for Cytokine-Induced Apoptosis, Science, 310:1646-1653 (2005).
Janes, K.A. et al., Cytokine-Induced Signaling Networks Prioritize Dynamic Range over Signal Strength, Cell, 135:343-354 (2008).
Jelle et al., "Transmission Spectra of an Electrochromic Window Consisting of Polyaniline, Prussian Blue and Tungsten Oxide," Electrochimica Acta, 38(11 ):1497-1500 (1993).
Jessel et al. Multiple and time-scheduled in situ DNA delivery mediated by B-cyclodextrin embedded in a polyelectrolyte multilayer, Jun. 6, 2006, PNAS, vol. 103, No. 23, pp. 8618-8621.
Jewell et al., "Multilayered polyelectrolyte assemblies as platforms for the delivery of DNA and other nucleic acid-based therapeutics" Adv. Drug Delivery Rev. 2008, 60, 979.
Jewell, C. M. et al. Release of Plasmid DNA from Intravascular Stents Coated with Ultrathin Multilayered Polyelectrolyte Films. Biomacromolecules 7, 2483-2491(2006).
Jewell, C. M., Zhang, J., Fredin, N. J. & Lynn ,D. M. Multilayered polyelectrolyte films promote the direct and localized delivery of DNA to cells. J. Controlled Release 106, 214-223 (2005).
Jiang et al., "Selective Deposition in Layer-by-Layer Assembly: Functional Graft," Langmuir, 16:8501-8509, (2000).
Johannsmann et al., "Effect of sample heterogeneity on the interpretation of QCM(-D) data: comparison of combined quartz crystal microbalance/atomic force microscopy measurements with finite element method modeling" Anal Chem. Dec. 1, 2008;80(23):8891-9.
Johansen, P. et al. Antigen kinetics determines immune reactivity. Proc. Natl. Acad. Sci. U. S. A. 105,5189-5194,doi:10.1073/pnas.0706296105 (2008).
John Wiley and Sons, Lysozyme: Substrate Structure, accessed Oct. 15, 2014, p. 1.
Kabanov, et al., "DNA Complexes with Polycations for the Delivery of Genetic Material inot Cells" Bioconjugate Chem. 6:7-20 (1995).
Kang, N. et al., Inhibition of EGFR signaling augments oridonin-induced apoptosis in human laryngeal cancer cells via enhancing oxidative stress conicident with activiation of both the intrinsic and extrinsic apoptotic pathways, Cancer Letters, 294:147-158 (2010).
Каргина, О.В. Сатораsц Еплнющиеся водорастворимые ионогенные ПОЛИМЕРЫ .: Kaprnha (Kargina) "Self-Splitted Water-Soluble Ionogenic Polymers" *Vysokomol. Soedin. Seriya A*, 28: 1139-1144, 1986. (with English abstract).
Katsuhiko, Sato, et al., "Layered Assemblies Composed of Sulfonated Cyclodextrin and Poly(allyamine)," Colloid & Polymer Science, 282:287-290 (2003).

(56) References Cited

OTHER PUBLICATIONS

Kearney CJ, Mooney DJ. Macroscale delivery systems for molecular and cellular payloads. Nat Mater 2013, 12(11): 1004-1017.
Keselowsky et al., "Integrin alpha(5) controls osteoblastic proliferation and differentiation responses to titanium substrates presenting different roughness characteristics in a roughness independent manner" J Biomed Mater Res A. Mar. 1, 2007;80(3):700-10.
Khan Y, Yaszemski MJ, Mikos AG, Laurencin CT. Tissue engineering of bone: material and matrix considerations. J Bone Joint Surg Am 2008, 90 Suppl 1: 36-42.
Khopade et al., "Electrostatically Assembled Polyelectrolyte/Dendrimer Multilayer Films as Ultrathin Nanoreservoirs," Nano Letters. 2:415, (2002).
Kim et al., "Enhanced memory responses to seasonal H1N1 influenza vaccination of the skin with the use of vaccine-coated microneedles" J Infect Dis 2010, 201, 190.
Kim et al., "Hydrogen-Bonding Layer-by-Layer-Assembled Biodegradable Polymeric Micelles as Drug Delivery Vehicles from Surfaces" ACS Nano 2008, 2, 386.
Kim et al., "MAD (multiagent delivery) nanolayer: delivering multiple therapeutics from hierarchically assembled surface coatings" Langmuir 2009, 25, 14086.
Kim, R., Recent Advances in Understanding the Cell Death Pathways Activated by Anticancer Therapy, Cancer, 1 03(8):1551-1560 (2005).
Kinsella CR, Jr., Bykowski MR, Lin AY, Cray JJ, Durham EL, Smith DM, et al. BMP-2-mediated regeneration of large-scale cranial defects in the canine: an examination of different carriers. Plast Reconstr Surg 2011, 127(5): 1865-1873.
Klopman et al., "Recent Methodologies for the Estimation of N-Octanol/Water Partition Coefficents and their Use in the Prediction of Membrane Transport Properties of Drugs," Mini-Reviews in Medicinal Chemistry. 5:127-133, (2005).
Krebs, M.R. et al. The formation of spherulites by6 amyloid fibrils of bovine insulin. Proc Natl Acad Sci USA 101, 14420-14424 (2004).
Krogman et al., Spraying asymmetry into functional membranes layer-by-layer Nat. Mater. 2009, 8, 512-518.
Krogman K, Cohen R, Hammond P, Rubner M, Wang B. Industrial-scale spray layer-by-layer assembly for production of biomimetic photonic systems. Bioinspiration & biomimetics 2013, 8(4): 045005.
Kukowska-Latallo, et al., "Efficient Transfer of Genetic Material into Manunalian Cells Using Starburst Polyamidoamine Dendrimers" Proc. Nat/. Acad. Sci. USA, 93: 4897-4902, 1996.
Kumar et al., "Patterning Self-Assembled Monolayers: Applications in Materials Science," Langmuir, 10:1498-1511 (1994).
Kwon et al., "Pseudopoly(amino acids): A Study of the Synthesis and Characterization of Poly(trans-4-hydroxy-N-acyi-L-proline esters)," Macromolecules, 22:3250-3255 (1989).
Landes CA, Ballon A, Roth C. Maxillary and mandibular osteosyntheses with PLGA and P(L/DL)LA implants: A 5-year inpatient biocompatibility and degradation experience. Plastic and Reconstructive Surgery 2006, 117(7): 2347-2360.
Langer, "Biomaterials in Drug Delivery and Tissue Engineering: One Laboratory's Experience," Ace. Chem. Res. 33:94-101, (2000).
Langer, "Selected Advances in Drug Delivery and Tissue Engineering," J. Control Release 62:7-11 (1999).
Lavan et al., "Small-scale systems for in vivo drug delivery," Nature Biotechnology 21 (1 0):1184-1191 (2003).
Lavos-Valereto et al., "In vitro and in vivo biocompatibility testing of Ti-6Al-7Nb alloy with and without plasma-sprayed hydroxyapatite coating" J Biomed Mater Res. 2001;58(6):727-33.
Lee K, Silva EA, Mooney DJ. Growth factor delivery-based tissue engineering: general approaches and a review of recent developments. Journal of The Royal Society Interface 2011, 8(55): 153-170.
Lee, J. S. et al. Gold, poly(_-amino ester) nanoparticles for small interfering RNA delivery. Nano Lett. 9, 2402-2406 (2009).
Lee, J.B., et al., "Self-assembled RNA interference microsponges for efficient siRNA delivery," Nature Materials, 11(4): 316-322 (2012).
Leguen et al., "Bioactive coatings based on polyelectrolyte multilayer architectures functionalized by embedded proteins, peptides or drugs" Biomol Eng., 24(1):33-41 (2007).
Liang et al., "The minimal functional sequence of protamine" Biochem. Biophys. Res. Commun. 2005, 336, 653.
Liao et al., "Response of rat osteoblast-like cells to microstructured model surfaces in vitro" Biomaterials. Feb. 2003;24(4):649-54.
Lighter, A.S. et al., Recent Advances in Radiation Oncology., New England Journal of Medicine, 332(6):371-379 (1995).
Lim, et al., "A Self-Destroying Polycationic Polymer: Biodegradable Poly(4-Hydroxy-LProline Ester)" JAm. Chem. Soc. 121: 5633-5639, 1999.
Lim, et al., "Cationic Hyperbranched Poly(amino ester): A Novel Class of DNA Condensing Molecule with Catioic Surface, Biodegradable Three-Dimensional Structure, and Tertiary Amine Groups in the Interior" J. Am. Chem. Soc. 2001, 123,2460-61.
Lim, et al., "Development of a Safe Gene Delivery System Using Biodegradable Polymer, Poly [a-(4-Aminobutyl-L-Glycolic Acid]" JAm. Chem. Soc. 122: 6524-6525, 2000.
Lin C-C, Anseth KS. PEG hydrogels for the controlled release of biomolecules in regenerative medicine. Pharmaceutical research 2009, 26(3): 631-643.
Linhardt, et al., "Free-Radical Synthesis ofPoly(2-Ethylacrylic Acid) Fractions of Low Polydispersity: Effects of Molecular Weight and Polydispersity on the pH-Dependent Conformational Transition in Aqueous Solution" Macromolecules. 32: 4457-4459 (1999).
Linhardt,• et al., "pH-Induced Fusion and Lysis ofPhosphatidylcholine Vesicles by Hydrophobic Polyelectrolyte Poly(2-ethylacrylic Acid)" Langmuir, 16: 122-127 (2000).
Liu, "Ultrathin Multilayered Films that Promote the Release of Two DNA Constructs with Separate and Distinct Release Profiles" Adv. Mater. 2008, 20 (pp. 4148-4153).
Livingstone et al., "Cationic Hyperbranched Poly(amino ester): A Novel Calss of DNA Condensing Molecule with Cationic Surface, Biodegradable Three-Dimensional Structure, and Tertiary Amine Groups in the Interior," J. Curr. Top. Med. Chem. 3: 1171-1192 (2003).
Lo H., et al., "Fabrication of controlled release biodegradable foams by phase separation," Tissue Eng. 1(1), 15-28 (1995).
Lopez, J.P. et al., Gefitinib Inhibition of Drug Resistance to Doxorubicin by Inactivating ABCG2 in Thyroid Cancer Cell Lines, Archives of Otolaryngology—Head & Neck Surgery, 133(10):1022-1027 (2007).
Luo, et al., "Synthetic DNA Delivery Systems" Nat. Biotechnol. 18: 33-37, 2000.
Lynn et al., "Degradable Poly(β-amino esters): Synthesis, Characterization, and Self-Assembly with Plasmid DNA," J. Am. Chem. Soc. 122:10761-10768, (2000).
Lynn et al., "pH-Responsive Polymer Microspheres: Rapid Release of Encapsulated Material Within the Range of Intracellular pH" Angewandte Chemie International Edition 2001, 40, 1707-1710.
Lynn, "Peeling Back the Layers: Controlled Erosion and Triggered Disassembly of Multilayered Polyelectrolyte Thin Films" Adv. Mater. 2007, 19 (pp. 4118-4130).
Lynn, et al., "Accelerated Discovery of Synthetic Transfection Vectors: Parallel Synthesis and Screening of a Degradable Polymer Library" Journal of the American Chemical Society 2001, 123, 8155-8156.
Lynn, et al., Construction of Degradable Thin Films via Layber-by-Layer Deposition of Polyelectrolytes: Fabrication, Characterization, and Application to Controlled Release, MIT Proposal 2001.
MacBeath, G., Protein microarrays and proteomics, Nature Genetics Supplement, 32:526-532 (2002).
Macdonald et al., "Release of a model protein from biodegradable self assembled films for surface delivery applications" J Control Release. Nov. 12, 2008;131(3):228-34.
MacDonald, et al.,"Tissue Integration of Growth Factor-Eluting Layer-by-Layer Polyelectrolyte Multilayer Coated Implants," Biomaterials, 32(5): 1446-1453 (2010).

(56) References Cited

OTHER PUBLICATIONS

Mansouri et al., "Modulating the release kinetics through the control of the permeability of the layer-by-layer assembly: a review" Expert Opin Drug Deliv. Jun. 2009;6(6):585-97.
Martin et al., "Solubility and Kinetic Release Studies of Naproxen and Ibuprofen in Soluble Epichlorohydrin-β-cyclodextrin Polymer," Supramolecular Chemistry. 18(8): 627-631, (2006).
Martinez, J., Patkaniowska, A., Urlaub, H., Luhrmann, R. & Tuschi, T. Single-stranded antisense siRNAs guide target RNA cleavage n RNAi. Cell 110, 563-574 (2002).
Martino MM, Tortelli F, Mochizuki M, Traub S, Ben-David D, Kuhn GA, et al. Engineering the growth factor microenvironment with fibronectin domains to promote wound and bone tissue healing. Sci Transl Med 2011, 3(100): 100ra189.
Mathiowitz, et al., "Polyanhydride Microspheres as Drug Carriers I. Hot-Melt Microencapsulation" J. Controlled Release, 5:13-22 (1987).
Mathiowitz, et al., "Polyanhydride Microspheres as Drug Carriers. II. Microencapsulation" J. Appl. Polymer Sci., 35: 755-774 (1988).
Mehrotra et al., "Time Controlled Protein Release from Layer-by-Layer Assembled Multilayer Functionalized Agarose Hydrogels" Adv Funct Mater. Jan. 22;20(2):247-58.
Mendelsohn et al., "Rational design of cytophilic and cytophobic polyelectrolyte multilayer thin films" Biomacromolecules. Jan.-Feb. 2003;4(1):96-106.
Michel, et al., "Printing meets lithography: Soft approaches to high-resolution patterning" IBM Journal of Research and Development, 45(5): 697-719 (2001).
Mikos A.G., et al., "Preparation and Characterization of Poly(L-Lactic Acid) Foams," Polymer 35(5): 1068-1077 (1994).
Mikszta et al., "Improved genetic immunization via micromechanical disruption of skin-barrier function and targeted epidermal delivery" Nat. Med. 2002, 8, 415.
Milano, G. et al., EGFR-targeting drugs in combination with cytotoxic agents: from bench to bedside, a contrasted reality, British Journal of Cancer, 99:1-5 (2008).
Miller, "Cationic Liposomes for Gene Therapy" Angew. Chem. Int. Ed. 37: 1769-1785, 1998.
Mistry AS, Mikos AG. Tissue engineering strategies for bone regeneration. Regenerative Medicine II. Springer, 2005, pp. 1-22.
Mizushima, N. et al., Methods in Mammalian Autophagy Research, Cell, 140:313-326 (2010).
Mok, H., Lee, S. H., Park, J. W. & Park, T. G. Multimeric small interfering ribonucleic acid for highly efficient sequence-specific gene silencing. Nature Mater. 9, 272-278 (2010).
Montesano, R. et al., Test for Malignant Transformation of Rat Liver Cells in Culture: Cytology, Growth in Soft Agar, and Production of Plasminogen Activator, Journal of the National Cancer Institute, 59(6):1651-1658 (1977).
Moor, A., et al., "Proteolytic Activity in Wound Fluids and Tissues Derived from Chronic Venous Leg Ulcers," Wound Repair and Regeneration, 17(6): 1067-1927 (2009).
Moran et al., Mixed protein carriers for modulating DNA release. Langmuir. Sep. 1, 2009;25(17):10263-70.
Morgillo, F. et al., Antitumor activity of bortezomib in human cancer cells with acquired resistance to anti-epidermal growth factor receptor tyrosine kinase inhibitors, Lung Cancer, 71 :283-290 (2011 ).
Moriguchi et al., "Synthesis of Ultrathin Films of Prussian Blue by Successive Ion Adsorption Technique," Chemistry Letters, 31 (3):31 0-311 (2002).
Morris, K.V., Chan, S.W., Jacobsen, S.E. & Looney, D.J. Small interfering RNA-induced transcriptional gene silencing in human cells. Science 305, 1289-1202 (2004).
Moskowitz et al., "The effectiveness of the controlled release of gentamicin from polyelectrolyte multilayers in the treatment of *Staphylococcus aureus* infection in a rabbit bone model" Biomaterials. Aug.;31(23):6019-30.
Mulligan, "The Basic Science of Gene Therapy" Science, 260: 926-932 (1993).

Murphy, et al., "A Combinatorial Approach to the Delivery of Efficient Cationic Peptoid Reagents for Gene Delivery", Proc. Natl. Acad. Sci. USA, 95: 1517-1522 (1998).
Neovius E, Engstrand T. Craniofacial reconstruction with bone and biomaterials: review over the last 11 years. Journal of plastic, reconstructive & aesthetic surgery : JPRAS 2010, 63(10): 1615-1623.
Neve, R.M. et al., A collection of breast cancer cell lines or the study of functionally distinct cancer subtypes, Cancer Cell, 10:515-527 (2006).
Nevins M, Giannobile WV, McGuire MK, Kao RT, Mellonig JT, Hinrichs JE, et al. Plateletderived growth factor stimulates bone fill and rate of attachment level gain: results of a large multicenter randomized controlled trial. J Periodontol 2005, 76(12): 2205-2215.
Newman et al., "Natural Products as Sources of New Drugs over the Period 1981-2002," Journal of Natural Products. 66:1022-1037 (2003).
Nguyen et al., "Extended Release Antibacterial Layer-by-Layer Films Incorporating Linear-Dendritic Block Copolymer Micelles," Chemistry of Materials. 19:5524-5530 (2007).
Niemiec et al., Nanoheterogeneous multilayer films with perfluorinated domains fabricated using the layer-by-layer method. Langmuir. Jul. 20;26(14)11915-20.
O'Donnell, et al., "Preparation ofMicrospheres by the Solvent Evaporation Technique" Adv. Drug Delivery Rev., 28:25-42, 1997.
Office Action for U.S. Appl. No. 10/280,268, entitled: "Methods of Making Decomposable Thin Films of Polyelectrolytes and Uses Thereofs", Dated: Jul. 6, 2005.
Office Action for U.S. Appl. No. 10/280,268, entitled: "Methods of Making Decomposable Thin Films of Polyelectrolytes and Uses Thereofs", Dated: Jun. 29, 2006.
Office Action for U.S. Appl. No. 10/280,268, entitled: "Methods of Making Decomposable Thin Films of Polyelectrolytes and Uses Thereofs", Dated: Nov. 2, 2004.
Office Action for U.S. Appl. No. 11/459,979, entitled: "Methods of Making Decomposable Thin Films of Polyelectrolytes and Uses Thereof", Dated: Jul. 23, 2010.
Office Action for U.S. Appl. No. 11/459,979, entitled: "Methods of Making Decomposable Thin Films of Polyelectrolytes and Uses Thereof", Dated: Oct. 29, 2009.
Office Action for U.S. Appl. No. 11/815,718, entitled: "Electrochemically Degradable Layer-By-Layer Thin Films", Dated: Mar. 26, 2012.
Office Action for U.S. Appl. No. 11/815,718, entitled: "Electrochemically Degradable Layer-By-Layer Thin Films", Dated: Mar. 27, 2014.
Office Action for U.S. Appl. No. 11/815,718, entitled: "Electrochemically Degradable Layer-By-Layer Thin Films", Dated: Nov. 27, 2012.
Office Action for U.S. Appl. No. 12/139,151, entitled: "Self Assembled Films for Protein and Drug Delivery Applications", Dated: Jun. 11, 2014.
Office Action for U.S. Appl. No. 12/139,151, entitled: "Self Assembled Films for Protein and Drug Delivery Applications", Dated: Jun. 20, 2012.
Office Action for U.S. Appl. No. 12/139,151, entitled: "Self Assembled Films for Protein and Drug Delivery Applications", Dated: Sep. 22, 2011.
Office Action for U.S. Appl. No. 12/542,267, entitled: "Controlled Delivery of Bioactive Agents From Decomposable Films", Dated: Aug. 17, 2012.
Office Action for U.S. Appl. No. 12/542,267, entitled: "Controlled Delivery of Bioactive Agents From Decomposable Films", Dated: Jun. 7, 2013.
Office Action for U.S. Appl. No. 12/542,267, entitled: "Controlled Delivery of Bioactive Agents From Decomposable Films", Dated: Mar. 31, 2014.
Office Action for U.S. Appl. No. 13/115,107, entitled: "Multilayer Coating Compositions, Coated Substrates and Methods Thereof", Dated: Apr. 17, 2014.
Office Action for U.S. Appl. No. 13/459,066, entitled: "Coating Compositions, Methods and Coated Devices ", Dated: Oct. 15, 2014.

(56) References Cited

OTHER PUBLICATIONS

Office Action for U.S. Appl. No. 13/459,069 entitled: "Coating Compositions, Methods and Coated Devices", Dated: Oct. 23, 2014.
Office Action for U.S. Appl. No. 13/695,836 entitled: "Drug Delivery Coating and Devices", Dated: Nov. 28, 2014.
Office Action for U.S. Appl. No. 13/746,902 entitled: "Compositions and Methods for Coating," Dated: Jan. 2, 2015.
Office Action for U.S. Appl. No. 13/869,015 entitled: "Stable Layer-By-Layer Coated Particles", Dated: Nov. 21, 2014.
Oh et al., "Stem cell fate dictated solely by altered nanotube dimension" Proc Natl Acad Sci U S A. Feb. 17, 2009;106(7):2130-5.
Okada, "One-and Three- Month Release Injectable Microspheres of the LH-RH Superagonist Leuprorelin Acetate" Adv. Drug Delivery Rev. 28: 43-70, 1997.
Oliva et al., "Antiproliferative Drug-Eluting Stents: Systematic Review of the Benefits and Estimate of Economic Impact," Rev Esp Cardiel, 57(7):617-628 (2004).
Papanas N, Maltezos E. Benefit-risk assessment of becaplermin in the treatment of diabetic foot ulcers. Drug safety : an international journal of medical toxicology and drug experience 2010, 33(6): 455-461.
Pareta et al., "An understanding of enhanced osteoblast adhesion on various nanostructured polymeric and metallic materials prepared by ionic plasma deposition" J Biomed Mater Res A. Mar. 1;92(3)1190-201.
Park et al., "Biodegradable polymer microneedles: fabrication, mechanics and transdermal drug delivery" J. Controlled Release 2005, 104, 51.
Park et al., "Osteoconductivity of hydrophilic microstructured titanium implants with phosphate ion chemistry" Acta Biomater. Jul. 2009;5(6):2311-21.
Park, J.-H., Allen, M. G. & Prausnitz ,M. R. Polymer microneedles for controlled-release drug delivery. Pharm. Res. 23, 1008-1019 (2006).
Pasco et al., "Characterization of a thermophilic L-glutamate dehydrogenase biosenor for amperometric determination of L-glutamate by flow injection analysis," Biosensors & Bioelectronics, 14:171-178 (1999).
Pashuck ET, Stevens MM. Designing Regenerative Biomaterial Therapies for the Clinic. Science translational medicine 2012, 4(160): 160sr164-160sr164.
Patil, m.L., et al., Surface-modified and internally Cationic polyamidoamine dendrimers for efficient siRNA delivery. Bioconjug Chem 19, 1396-1403 (2008).
Pawson, T. et al., Network medicine., FEBS Letters, 582:1266-1270 (2008).
Pearton et al., "Gene delivery to the epidermal cells of human skin explants using microfabricated microneedles and hydrogel formulations" Pharm. Res. 2008, 25, 407.
Peer, D., P. Zhu, C. V. Carman, J. Lieberman, and M. Shimaoka, Selective gene silencing in activated leukocytes by targeting siRNAs to the integrin lymphocyte function-associated antigen-1. Proc Nat! Acad Sci USA, 2007. 104(10): p. 4095-4100.
Peer, D., Park, E. J., Morishita, Y., Carman, C. V. & Shimaoka, M. Systemic leukocyte-directed siRNA delivery revealing cyclin D1 as an anti-inflammatory target. Science 319, 627-630 (2008).
Peerce et al., "Polymer Films on Electrodes, Part III. Digital Simulation Model for Cyclic Voltammetry of Electroactive Polymer Film and Electrochemistry of Poly(vinylferrocene) on Platinum," J. Electroanal. Chem, 114:89-115 (1980).
Perou, C.M. et al., Molecular portraits of human breast tumours, Nature, 406:747-752 (2000).
Petrie et al., "The effect of integrin-specific bioactive coatings on tissue healing and implant osseointegration" Biomaterials. Jul. 2008;29(19):2849-57.
Pfeifer et al., "Formulation and surface modification of poly(ester-anhydride) micro- and nanoshperes," Biomaterials, 26:117-124 (2005).

Picart et al., "Molecular basis for the explanation of the expotential growth of polyelectrolyte multilayers" PNAS 99(20)12531-12535 (2002).
Place ES, Evans ND, Stevens MM. Complexity in biomaterials for tissue engineering. Nat Mater 2009, 8(6): 457-470.
Poerner et al., "Drug-coated stents," Minimally Invasive Therapy & Allied Technologies 11(4):185-192 (2002).
Porcel et al., "From exponential to linear growth in polyelectrolyte multilayers" Langmuir. Apr. 25, 2006;22(9):4376-83.
Porcel et al., "Influence of the polyelectrolyte molecular weight on exponentially growing multilayer films in the linear regime" Langmuir. Feb. 13, 2007;23(4)1898-904.
Porter JR, Ruckh TT, Popat KC. Bone tissue engineering: a review in bone biomimetics and drug delivery strategies. Biotechnology Progress 2009, 25(6): 1539-1560.
Prausnitz, "Microneedles for transdermal drug delivery" Adv. Drug Delivery Rev. 2004, 56, 581.
Prausnitz, et al., "Transdermal drug delivery" Nat. Biotechnol., 26: 1261 (2008).
Pruss-Ustun et al., WHO Environmental Burden of Disease Series, World Health Organization, 2003.
Putnam et al., "Poly(4-hydroxy-L-proline ester): Low-Temperature Polycondensation and Plasmid DNA Complexation," Macromolecules, 32:3658-3662 (1999).
Qiu, et al., "Studies on the Drug Release Properties of Polysaccharide Multi layers Encapsulated Ibuprofen Microparticles" Langmuir 17: 5375-5380 (2001).
Quan et al., "Stabilization of influenza vaccine enhances protection by microneedle delivery in the mouse skin" PLoS One 2009, 4, e7152.
Quarles et al., "Distinct proliferative and differentiated stages of murine MC3T3-E1 cells in culture: an in vitro model of osteoblast development" J Bone Miner Res. Jun. 1992;7(6):683-92.
Rajan et al., "Eiectrochromism in the Mixed-Valence Hexacyanides. 2. Kinetics of the Reduction of Ruthenium Purple and Prussian Blue," J. Phys. Chem., 86:4361-4368 (1982).
Ramaswamy et al., "Sphene ceramics for orthopedic coating applications: an in vitro and in vivo study" Acta Biomater. Oct. 2009;5(8):3192-204.
Rao, et al., "Poly (Butaneodiol Spermate): A Hydrolytically Labile Polyester-Based Nitric Oxide Carrier" J. Bioactive and Compatible Polymers 14: 54-63, 1999.
Rausch-fan et al., "Differentiation and cytokine synthesis of human alveolar osteoblasts compared to osteoblast-like cells (MG63) in response to titanium surfaces" Dent Mater. Jan. 2008;24(1):102-10.
Razzacki et al., "Integrated microsystems for controlled drug delivery," Advanced Drug Delivery Reviews, 56:185-198 (2004).
Richards, K. E., Williams, R. C. & Calendar, R. Mode of DNA packing within bacteriophage heads. J. Mol. Biol. 78, 255-259 (1973).
Richert et al., "Cell interactions with polyelectrolyte multilayer films" Biomacromolecules. Nov.-Dec. 2002;3(6):1170-8.
Roach et al., "Interpretation of protein adsorption: surface-induced conformational changes" J Am Chem Soc. Jun. 8, 2005;127(22):8168-73.
Roach et al., "Modern biomaterials: a review—bulk properties and implications of surface modifications" J Mater Sci Mater Med. Jul. 2007;18(7):1263-77.
Roberts, et al., "Preliminary Biological Evaluation ofPolyamidoamine (P AMAM) Starburst TM Dendrimers" J. Biomed. Mater. Res. 30: 53-65, 1996.
Robin et al., "The Color and Electronic Configurations of Prussian Blue," Electronic Configurations of Prussian Blue, 1( 2):337-342 (1962).
Rohanizadeh, R., et al., "Gelatin Sponges (Gelfoam®) as a scaffold for Osteoblasts", J. Mater. Sci. Mater Med., 19:1173-1182 (2008).
Rusnak, D.W. et al., Assessment of epidermal growth factor receptor (EGFR, ErbB1) and HER2 (ErbB2) protein expression levels and response to lapatinib (Tykerb®, GW572016) in an expanded panel of human normal and tumour cell lines, Cell Proliferation, 40: 580-594 (2007).
Sachs, K. et al., Casual Protein-Signaling Networks Derived from Multiparameter Single-Cell Data, Science, 308:523-529 (2005).

(56) References Cited

OTHER PUBLICATIONS

Saha et al., "Designing synthetic materials to control stem cell phenotype" Curr Opin Chem Biol. Aug. 2007;11(4):381-7.
Sallusto, F., Geginat, J. & Lanzavecchia, A. Central memory and effector memory T cell subsets: Function, generation, and maintenance. Annu. Rev. Immunol. 22 ,145-163, doi:10.1146/annurev.immunol.22.012103.104102 (2004).
Samuel, R. E. et al. Osteoconductive protamine-based polyelectrolyte multilayer functionalized surfaces. Biomoteriols 32,1491-1502,do1:10.1016/j.biomaterials.2011.06.032 (2011).
Sanford, "The Biolistic Process" Trends Biotechnol. 6:288-302, 1988.
Santini et al., "Microchips as Controlled Drug-Delivery Devices," Angew. Chem. Int. Ed., 39:2396-2407 (2000).
Santini et al., "Microchips for drug delivery," Abstracts of Papers of the American Chemical Society, 219(174):U34-U34 (2000).
Sapi, E. et al., Ets-2 Transdominant Mutant Abolishes Anchorage-independent Growth and Macrophage Colony-stimulating Factor-stimulated Invasion by BT20 Breast Carcinoma Cells, Cancer Research, 58:1027-1033 (1998).
Schaffer, et al., "Vector Unpacking as a Potential Banier for Receptor-Mediated Polyplex Gene Delivery" Biotechnol. Bioeng., 61: 598-606 (000).
Schechter, A.L. et al., The neu oncogene: an erb-8-related gene encoding a 185,000-Mr tumour antiQen, Nature, 312:513-516 (1984).
Schlenoff, "Retrospective on the future of polyelectrolyte multilayers" Langmuir. Dec. 15, 2009;25(24):14007-10.
Schmidt et al., "Electrochemically controlled swelling and mechanical properties of a polymer nanocomposite" ACS Nano. Aug. 25, 2009;3(8):2207-16.
Schmitz JP, Hollinger JO. The Critical Size Defect as an Experimental-Model for Craniomandibulofacial Nonunions. Clinical Orthopaedics and Related Research 1986(205): 299-308.
Schuler "Decomposable Hollow Biopolymer-Based Capsules" Biomacromolecules, vol. 2, 2001 921-26.
Schwarz et al., "Potential of chemically modified hydrophilic surface characteristics to support tissue integration of titanium dental implants" J Biomed Mater Res B Appl Biomater. Feb. 2009;88(2):544-57.
Schweikl, et al., "Triethylene Glycol Dimethacrylate Induces Large Deletions in the Hprt Gene of V79 Cells" Mutat. Res. 438: 71-78 (1999).
Seeman, N. C. Nanomaterials based on DNA. Annu. Rev. Biochem. 79, 65-87 (2010).
Semple, S. C. et al. Rational design of cationic lipids for siRNA delivery. Nature Biotechnol. 28, 172-176 (2010).
Sengupta, S. et al. Temporal targeting of tumor cells and neovasculature with a nanoscale delivery system, Nature, 436:568-572 (2005).
Seo et al., "Effect of the layer-by-layer (LbL) deposition method on the surface morphology and wetting behavior of hydrophobically modified PEO and PAA LbL films" Langmuir. Aug. 5, 2008;24(15):7995-8000.
Sevecka, M. et al., State-based discovery: a multidimensional screen for small-molecule modulators of EGF signaling, Nature Methods, 3(1 0):825-831 (2006).
Seyhan, A. A., et al., "RNA interference from Multimeric shRNSs generated by rolling circle transcription," Oligonucleotides, 16(4): 353-363 (2006).
Shah NJ, Hyder MN, Moskowitz JS, Quadir MA, Morton SW, Seeherman HJ, et al. Surface-Mediated Bone Tissue Morphogenesis from Tunable Nanolayered Implant Coatings. Science Translational Medicine 2013, 5(191).
Shiratori et al., "pH-Dependent Thickness Behavior of Sequentially Adsorbed Layers of Weak Polyelectrolytes," Macromolecules, 33:4213-4219 (2000).
Shukla et al., "Controlling the release of peptide antimicrobial agents from surfaces" Biomaterials. Mar. 2010;31(8):2348-2357.

Shukla et al., "Tunable Vancomycin Releasing Surfaces for Biomedical Applications", Small Nano Mirco, 2010, 21 (6), 2392-2404.
Shutava et al., "Layer-by-Layer-Coated Gelatin Nanoparticles as a Vehicle for Delivery of Natural Polyphenols" ACS Nano. Jul. 28, 2009;3(7):1877-85.
Singh, et al., "Cationic Microparticles: A Potent Delivery System for DNA Vaccines" Proc. Nat/. Acad. Sci. USA, 97: 811-816,2000.
Slamon, D.J. et al., Human Breast Cancer: Correlation of Relapse and Survival with Amplification of the HER-2/neu Oncogene, Science, 235:177-182 ( 1987).
Smiell JM, Wieman TJ, Steed DL, Perry BH, Sampson AR, Schwab BH. Efficacy and safety of becaplermin (recombinant human platelet-derived growth factor-BB) in patients with nonhealing, lower extremity diabetic ulcers: a combined analysis of four randomized studies. Wound repair and regeneration : official publication of the Wound Healing Society [and] The European Tissue Repair Society 1999, 7(5): 335-346.
Smith et al., "Layer-by-Layer Platform Technology for Small-Molecule Delivery", Anqew.Chem.Int.Ed., 2009, 48, 8974-8977, with English Abtract.
Smith, K. A. et al. Enhancing ONA vaccination by sequential injection of lymph nodes with plasmid vectors and peptides. Vaccine 27,2603-2615,doi:10.1016/j.vaccine.2009.02.038 (2009).
Smith, K. A. et al. Multivalent immunity targeting tumor-associated antigens by intra-lymph node DNA-prime ,peptide-boost vaccination. Cancer Gene Ther. 18, 63-76,doi:10.1038/cgt.2010.45 (2011).
Song, Jie, et al., "Growth of endothelial cell on the surface of intravascular sent material: Bionic construction of bioactive extracellular matrix", Journal of Clinical Rehabilitative Tissue Engineering Research, Oct. 22, 2009, 13(43), 8425-8431.
Sordella, R. et al., Gefitinib-Sensitizing EGFR Mutations in Lung Cancer Activate AntiApoptotic Pathways, Science, 305:1163-1167 (2004).
Spicer PP, Kretlow JD, Young S, Jansen JA, Kasper FK, Mikos AG. Evaluation of bone regeneration using the rat critical size calvarial defect. Nature protocols 2012, 7(10): 1918-1929.
Stevens MM. Biomaterials for bone tissue engineering. Materials Today 2008, 11(5): 18-25.
Strathmann H. Membrane separation processes: current relevance and future opportunities. AIChE Journal 2001, 47(5): 1077-1087.
Stubbs, Milton T., et al, Eur. J. Biochem. 2006 (1992), pp. 187-195.
Su et al., "Layer-by-layer-assembled multilayer films for transcutaneous drug and vaccine delivery" ACS Nano 2009, 3, 3719-3729.
Subramanian, A. et al., Gene set enrichment analysis: A knowledge-based approach for interpreting genome-wide expression profiles, Proceedings of the National Academy of Sciences of the USA, 102(43):15545-15550 (2005).
Sullivan, S. P.,Murthy, N. & Prausnitz ,M. R. Minimally invasive protein delivery with rapidly dissolving polymer microneedles. Adv. Mater. 20, 933-938 (2008).
Sun, T. et al., Activation of Multiple Proto-oncogenic Tyrosine Kinases in Breast Cancer via Loss of the PTPN12 Phosphatase, Cell, 144:703-718 (2011 ).
Tang, et al., "Adhesion and endothelialization of endothelial cells on the surface of endovascular stents by the novel rotational culture of cells," Applied Surface Science, 255:315-319 (2008).
Tang, et al., "In Vitro Gene Delivery by Degraded Polyamidoamine Dendrimers" Bioconjugate Chem. 7:703-714, 1996.
Taratula, O. et al. Surface-engineered targeted PPI dendrimer for efficient intracellular and intratumoral siRNA delivery. J. Control. Release 140, 284-293 (2009).
Tetko et al., "Virtual Computational Chemistry Laboratory-design and description," Computer-Aided Mol. Des. 19: 453-463 (2005).
Thompson et al., "Biochemical functionalization of polymeric cell substrata can alter mechanical compliance" Biomacromolecules. Jun. 2006;7(6):1990-5.
Thompson et al., "Tuning compliance of nanoscale polyelectrolyte multilayers to modulate cell adhesion" Biomaterials. Dec. 2005;26(34):6836-45.
Tijsterman, M., Ketting, R. F. & Plasterk, R. H. The genetics of RNA silencing. Annu. Rev. Genet. 36, 489-519 (2002).

(56) References Cited

OTHER PUBLICATIONS

Toniolo et al., "II. Circular dichroism study of the three main components of clupeine" Biochim Biophys Acta. Feb. 26, 1979;576(2):429-39.
Trubetskoy, V. S., Loomis, A., Hagstrom, J. E., Budker, V. G. & Wolff, J. A. Layer-by-layer deposition of oppositely charged polyelectrolytes on the surface of condensed DNA particles. Nucleic Acids Res. 27, 3090-3095 (1999).
Turner, J.G. et al., ABCG2 expression, function, and promoter methylation in human multiple myeloma, Blood, 108(12):3881-3889 (2006).
Uhrich et al., "Polymeric Systems for Controlled Drug Release," Chem. Rev. 99:3181-3198 (1999).
Uhrich, K., "Hyperbranched Polymers for Drug Delivery" Trends Polym. Sci. 5: 388-393 (1997).
van de Wetering, et al., "Structure-Activity Relationships of Water-Soluble Cationic Methacrylate/Methacrylamide Polymers for Non viral Gene Delivery" Bioconjugate Chem. 10: 589-597, 1999.
Vazquez et al., "Variation of polyelectrolyte film stiffness by photo-cross-linking: a new way to control cell adhesion" Langmuir. Apr. 9, 2009;25(6):3556-63.
Vittal et al., "Surfactant Promoted Enhancement on Electrochemical and Electrochromic Properties of Films of Prussian Blue and Its Analogs," Journal of The Electrochmical Socitey, 146(2):786-793 (1999).
Vo TN, Kasper FK, Mikos AG. Strategies for controlled delivery of growth factors and cells for bone regeneration. Adv Drug Deliv Rev 2012, 64(12): 1292-1309.
Wang D., et al., "Synthesis and evaluation of water-soluble polymeric bone-targeted drug delivery systems," Bioconjugate Chemistry 14(5): 853-859 (2003).
Wang et al., "A Novel Biodegradable Gene Carrier Based on Polyphoophoester," J. Am. Chem. Soc. 123:9480-9481 (2001).
Wang, P. M., Cornwell, M., Hill, J. & Prausnitz ,M. R. Precise Microinjection into Skin Using Hollow Microneedles. J. Invest. Dermatol. 126,1080-1087,doi:10.1038/sj.jid.5700150 (2006).
Warner, T.D., et al., "Nonsteroid Drug Selectives for Cyclo-Oxygenase-1 Rather Than Cyclo-Oxygenase-2 are associated with Human Gastrointestinal Toxicity: A full in vitro Analysis," Proceedings of the National Academy of Sciences of the United States of America, 96: 9966 (1999).
Watts NB, Diab DL. Long-Term Use of Bisphosphonates in Osteoporosis. J Clin Endocr Metab 2010, 95(4): 1555-1565.
Wick, D. A., Martin, S. D., Nelson, B. H. & Webb ,J. R. Profound CD8+ T cell immunity elicited by sequential daily immunization with exogenous antigen plus the TLR3 agonist poly(I:C). Vaccine 29, 984-993, doi:10.1016/j.vaccine.2010.11.036 (2011).
Wikipedia, Heparin, accessed Oct. 15, 2014, pp. 1-18.
Will J, Melcher R, Treul C, Travitzky N, Kneser U, Polykandriotis E, et al. Porous ceramic bone scaffolds for vascularized bone tissue regeneration. Journal of Materials Science: Materials in Medicine 2008, 19(8): 2781-2790.
Winer, E.P. et al., Optimizing Treatment of "Triple-Negative" Breast Cancer. SABCS 2007: Improving Outcomes in Advanced and Meta-static Breast Cancer, http://www.medscape.org/viewarticle/569483 (2007).
Woeblecke, H. et al., Reversal of breast cancer resistance protein-mediated drug resistance by tryprostatin A, International Journal of Cancer, 107:721-728 (2003).
Wood et al., "Controlling Interlayer Diffusion to Achieve Sustained, Multiagent Delivery from Layer-by-Layer Thin Films," Proceedings of the National Academy of Sciences of the United States of America, 103(27):10207-10212 (2006).
Wood et al., "Tunable drug release from hydrolytically degradable layer-by-layer thin films" Langmuir. Feb. 15, 2005;21(4)1 603-9.
Wood, E.R. et al., A Unique Structure for Epidermal Growth Factor Receptor Bound to GW572016 (Lapatinib): Relationships among Protein Conformation, Inhibitor Off-Rate, and Receptor Activity in Tumor Cells, Cancer Research, 64:6652-6659 (2004).
Woodruff MA, Lange C, Reichert J, Berner A, Chen F, Fratzl P, et al. Bone tissue engineering: from bench to bedside. Materials Today 2012, 15(10): 430-435.
Written Opinion for PCT/US2014/022107, entitled: Compositions and Methods for Nucleic Acid Delivery, Date of mailing: Jun. 5, 2014.
Written Opinion PCT/US2014/018284, entitled:Nucleic Acid Particles, Methods and Use Thereof, Date of mailing: Jul. 30, 2014.
Yang, et al., "A New Approach to Identifying Genotoxic Carcinogens: p53 Induction as an Indicator of Genotoxic Damage" Carcinogenesis, 19: P1117-P1125, 1998.
Yoon, C-H. et al., Activation of p38 Mitogen-Activated Protein Kinase Is Required for Death Receptor-Independent Caspase-8 Activation and Cell Death in Response to Sphingosine, Molecular Cancer Research, 7(3):361-370 (2009).
Zauner, et al., "Polylysine-Based Transfection Systems Utilizing Receptor-Mediated Delivery" Adv. Drug. Del. Rev. 30: 97-113, 1998.
Zhang, J., et al., "Multilayered Thin Films that Sustain the Release of Functional DNA under Physiological Conditions," Langmuir, 20(19): 8015-8021 (2004).
Zhang,J., Fredin, N. J., Janz, J. F. , Sun, B. & Lynn, D. M. Structure/property relationships in erodible multilayered films: influence of polycation structure on erosion profiles and the release of anionic polyelectrolytes. Langmuir 22, 239-245, doi:10.1021/la052360b (2006).
Zheng et al., "Controlling cell attachment selectively onto biological polymer-colloid templates using polymer-on-polymer stamping" Langmuir. Aug. 17, 2004;20(17):7215-22.
Zhou, et al., "Preparation of Poly(L-serine ester): A Structural Analogue of Conventional Poly(L-serine)" Macromolecules, 23: 3399-3406, 1990.

\* cited by examiner

Engineering Strategy 1

Engineering Strategy 2

SEQUENCE LISTING

```
<160> NUMBER OF SEQ ID NOS: 3

<210> SEQ ID NO 1
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atagtgagtc gtattaacgt accaacaact tacgctgagt acttcgatta cttgaatcga      60
agtactcagc gtaagtttag aggcatatcc ct                                    92

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 2
taatacgact cactataggg at                                                    22

<210> SEQ ID NO 3
<211> LENGTH: 736
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
agggauaugc cucuaaacuu acgcugagua cuucgauuca aguaaucgaa guacucagcg           60
uaaguuguug guacguuaau acgacucacu auagggauau gccucuaaac uuacgcugag          120
uacuucgauu caaguaaucg aaguacucag cguaaguugu ugguacguua auacgacuca          180
cuauagggau augccucuaa acuuacgcug aguacuucga uucaaguaau cgaaguacuc          240
agcguaaguu guugguacgu uaauacgacu cacuauaggg auaugccucu aaacuuacgc          300
ugaguacuuc gauucaagua aucgaaguac ucagcguaag uuguugguac guuaauacga          360
cucacuauag gauaugccu cuaaacuuac gcugaguacu ucgauucaag uaaucgaagu           420
acucagcgua aguuguuggu acguuaauac gacucacuau agggauaugc cucuaaacuu          480
acgcugagua cuucgauuca aguaaucgaa guacucagcg uaaguuguug guacguuaau          540
acgacucacu auagggauau gccucuaaac uuacgcugag uacuucgauu caaguaaucg          600
aaguacucag cguaaguugu ugguacguua auacgacuca cuauagggau augccucuaa          660
acuuacgcug aguacuucga uucaaguaau cgaaguacuc agcguaaguu guugguacgu          720
uaauacgacu cacuau                                                         736
```

NUCLEIC ACID PARTICLES, METHODS AND USE THEREOF

RELATED APPLICATIONS

This application is a continuation of U.S. application Ser. No. 14/190,983, filed Feb. 26, 2014, which claims the benefit of U.S. Provisional Application No. 61/769,731, filed on Feb. 26, 2013. The entire teachings of the above application(s) are incorporated herein by reference.

INCORPORATION BY REFERENCE OF MATERIAL IN ASCII TEXT FILE

This application incorporates by reference the Sequence Listing contained in the following ASCII text file:

a) File name: MTU-25502SequenceListing.txt; created Apr. 3, 2017, 3 KB in size.

GOVERNMENT SUPPORT

This invention was made with government support under Grant No. DMR-0705234 awarded by the National Science Foundation. The government has certain rights in the invention.

BACKGROUND

RNA interference (RNAi) is a powerful tool for suppressing gene expression, and much research has been directed at efforts to develop an efficient delivery method for small interference RNA (siRNA). Conventional complexation or encapsulation of siRNA with polymers or lipids can often require multi-step synthesis of carriers or relatively ineffectual encapsulation processes; furthermore, such approaches often involve introducing a significant amount of an additional component, which can lead to greater potential for immunogenic response or toxicity. In addition, the amount of siRNA per carrier is limited due to the rigidity of double stranded siRNA, low surface charge of individual siRNA, and low loading efficiency, making RNAi encapsulation particularly challenging. Furthermore, RNAi requires specialized synthesis and is often available in small quantities at high cost, making it a very costly cargo that is delivered with fairly low efficiency carriers. Thus, there is a continuing need for new insights on improved technologies for efficient delivery of nucleic acids such as siRNA.

SUMMARY

The present invention, among other things, describes particles including a core of self-assembled one or more nucleic acid molecules. In some embodiments, nucleic acid molecules within a particle core are formed via elongation by rolling circle amplification (RCA) and/or rolling circle transcription (RCT). In some embodiments, provided particles may contain a core that is coated by a film so that the particles are condensed to achieve a smaller particle size. Provided compositions and methods can be particularly useful for delivery of high loads of nucleic acids, optionally with any other agents.

DEFINITIONS

In order for the present disclosure to be more readily understood, certain terms are first defined below.

In this application, the use of "or" means "and/or" unless stated otherwise. As used in this application, the term "comprise" and variations of the term, such as "comprising" and "comprises," have their understood meaning in the art of patent drafting and are inclusive rather than exclusive, for example, of additional additives, components, integers or steps. As used in this application, the terms "about" and "approximately" have their art-understood meanings; use of one vs the other does not necessarily imply different scope. Unless otherwise indicated, numerals used in this application, with or without a modifying term such as "about" or "approximately", should be understood to cover normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated reference value unless otherwise stated or otherwise evident from the context (except where such number would exceed 100% of a possible value).

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biodegradable": As used herein, the term "biodegradable" is used to refer to materials that, when introduced into cells, are broken down by cellular machinery (e.g., enzymatic degradation) or by hydrolysis into components that cells can either reuse or dispose of without significant toxic effect(s) on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component and/or into fragments thereof (e.g., into monomeric or submonomeric species). In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Nucleic acid": The term "nucleic acid" as used herein, refers to a polymer of nucleotides. In some embodiments, nucleic acids are or contain deoxyribonucleic acids (DNA); in some embodiments, nucleic acids are or contain ribonucleic acids (RNA). In some embodiments, nucleic acids include naturally-occurring nucleotides (e.g., adenosine, thymidine, guanosine, cytidine, uridine, deoxyadenosine, deoxythymidine, deoxyguanosine, and deoxycytidine). Alternatively or additionally, in some embodiments, nucleic acids include non-naturally-occurring nucleotides including, but not limited to, nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups. In some embodiments, nucleic acids include phosphodiester backbone linkages; alternatively or additionally, in some embodiments, nucleic acids include one or more non-phosphodiester backbone linkages such as, for example, phosphorothioates and 5'-N-phosphoramidite linkages. In some embodiments, a nucleic acid is an oligonucleotide in that it is relatively short (e.g., less that about 5000, 4000, 3000, 2000, 1000, 900, 800, 700, 600, 500, 450, 400, 350, 300, 250, 200, 150, 100, 90, 80, 70, 60, 50, 45, 40, 35, 30, 25, 20, 15, 10 or fewer nucleotides in length)

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polyelectrolyte": The term "polyelectrolyte", as used herein, refers to a polymer which under a particular set of conditions (e.g., physiological conditions) has a net positive or negative charge. In some embodiments, a polyelectrolyte is or comprises a polycation; in some embodiments, a polyelectrolyte is or comprises a polyanion. Polycations have a net positive charge and polyanions have a net negative charge. The net charge of a given polyelectrolyte may depend on the surrounding chemical conditions, e.g., on the pH.

"Polypeptide": The term "polypeptide" as used herein, refers to a string of at least three amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/dadgrp/Unnatstruct.gif, which displays structures of non-natural amino acids that have been successfully incorporated into functional ion channels) and/or amino acid analogs as are known in the art may alternatively be employed). In some embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g, modified sugars such as 2"-fluororibose, 2"-deoxyribose, and hexose).

"Reference nucleic acid": The term "reference nucleic acid", as used herein, refers to any known nucleic acid molecule with which a nucleic acid molecule of interest is compared.

"Sequence element": The term "sequence element", as used herein, refers to a discrete portion of nucleotide sequence, recognizable to one skilled in the art. In many embodiments, a sequence element comprises a series of at least 3, 4, 5, 6, 7, 8, 9, 10, 11, 12, 13, 14, 15, 116, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10,000 or more contiguous nucleotides in a polymer. In some embodiments, a sequence element is recognizable because it is found in a different nucleic acid molecule, with which a nucleic acid molecule of interest is being compared. Those of ordinary skill in the art are well aware of methodologies and resources available for the comparison of nucleic acid sequences. In some embodiments, a nucleic acid molecule of interest has a nucleotide sequence that is selected or designed to contain, or otherwise contains, one or more particular sequence elements that is/are found in one or more (optionally predetermined) reference or source nucleic acids.

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present application.

"Source nucleic acid": The term "source nucleic acid" is used herein to refer to a known nucleic acid molecule whose nucleotide sequence includes at least one sequence element of interest. In some embodiments, a source nucleic acid is a natural nucleic acid in that it occurs in a context (e.g., within an organism) as exists in nature (e.g., without manipulation by the hand of man). In some embodiments, a source nucleic acid is not a natural nucleic acid in that its nucleotide sequences includes one or more portions, linkages, or elements that do not occur in the same arrangement in nature and/or were designed, selected, or assembled through action of the hand of man.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease.

BRIEF DESCRIPTION OF THE DRAWING

The Drawing, comprised of several Figures, is for illustration purposes only, not for limitation.

DETAILED DESCRIPTION OF CERTAIN EMBODIMENTS

Figure 1:
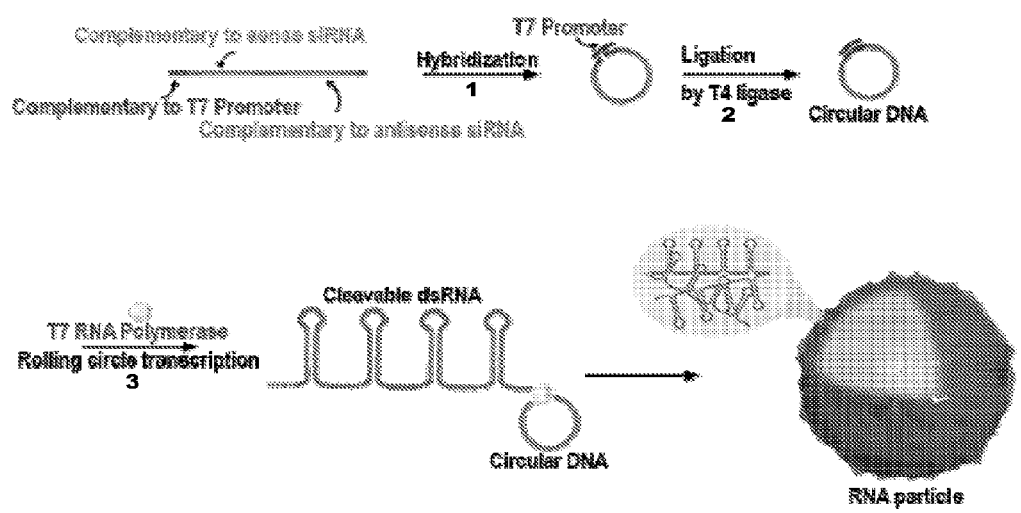
FIG. 1. Schematic drawing of the process of rolling circle transcription (RCT) for the self-assembled RNAi-microsponge used in accordance with certain embodiments of the present invention. To perform RCT, circular DNA needs to be synthesized first. Linear ssDNA that includes antisense and sense sequences of anti-luciferase siRNA is hybridized with equal molar of short DNA strand containing T7 promoter sequence. The nick in the circular DNA was chemically closed by T4 DNA ligase. By RCT of the closed circular DNA, multiple tandem repeats of hairpin RNA structures from both antisense and sense sequences are generated to be able to form spherical sponge-like structure.

The present invention, among other things, describes compositions of nucleic acid particles and methods and uses thereof.

Particles

Particles used in accordance with various embodiments of the present disclosure can contain a particle core, which can optionally be coated by a film. Upon coating, a particle can be converted from a first configuration to a second configuration.

In some embodiments, the greatest dimension of a particle (in its first or second configuration) may be greater or less than 5 μm, 2 μm, 1 μm, 800 nm, 500 nm, 200 nm, 100 nm, 90 nm, 80 nm, 70 nm, 60 nm, 50 nm, 40 nm, 30 nm, 20 nm, 10 nm, or even 5 nm. In some embodiments, the greatest dimension a particle (in its first or second configuration) may be in a range of any two values above. In some embodiments, a particle in a first configuration has the greatest dimension in a range of about 5 μm to about 2 μm or about 2 μm to about 1 μm. In some embodiments, a particle in a second configuration has the greatest dimension in may be in a range of about 500 nm to about 200 nm, about 200 nm to about 100 nm or about 100 nm to about 50 nm. In some embodiments, a particle can be substantially spherical. In some embodiments, the dimension of a particle is a diameter, wherein the diameter can be in a range as mentioned above.

In various embodiments, a particle described herein can comprise a particle core, a coating film (including one or more layers; in some embodiments one or more polyelectrolyte layers), and one or more agents such as diagnostic, therapeutic and/or targeting agents.

Nucleic Acid-Containing Core

A particle core can consist of or include one or more nucleic acid molecules. In some embodiments, a core is comprised of a plurality of nucleic acid molecules. Individual nucleic acid molecules within a core can have different nucleic acid sequences or substantially the same nucleic acid sequence. In some embodiments, nucleic acid molecule(s) within a core have sequences that share at least one common sequence element.

In some embodiments, at least one nucleic acid molecule in a core has a nucleotide sequence that comprises multiple copies of at least a first sequence element. In some embodiments, at least one nucleic acid molecule in a core has a nucleotide sequence that comprises multiple copies of each of at least a first and a second sequence element. In some embodiments, at least one nucleic acid molecule has a nucleotide sequence that comprises alternating copies of the first and second sequence elements. In some embodiments, at least one nucleic acid molecule has a nucleotide sequence that comprises multiple copies of each of three or more sequence elements.

In some embodiments, at least one nucleic acid molecule has a nucleotide sequence that includes one or more sequence elements found in a natural source. In some embodiments, at least one nucleic acid molecule has a nucleotide sequence that includes a first sequence element that is found in a first natural source and a second sequence element that is found in a second natural source. The first and second natural sources can be the same or difference.

In some embodiments, at least one nucleic acid molecule has a nucleotide sequence that represents an assemblage of sequence elements found in one or more source nucleic acid molecules. In some embodiments, at least one nucleic acid molecule has a nucleotide sequence that represents an assemblage of at least two different sequence elements found in two different source nucleic acid molecules.

In some embodiments, nucleic acid molecule(s) within a core have nucleotide sequences that fold into higher order structures (e.g., double and/or triple-stranded structures). In some embodiments, nucleic acid molecule(s) within a core have nucleotide sequences that comprise two or more complementary elements. In some embodiments, such complementary elements can form one or more (optionally alternative) stem-loop (e.g., hairpin) structures. In some embodiments, nucleic acid molecule(s) within a core have nucleotide sequences that include one or more portions that remain single stranded (i.e., do not pair intra- or intermolecularly with other core nucleic acid sequence elements).

In some embodiments, at least one nucleic acid molecules in a core contains at least one cleavage site. In some embodiments, a cleavage site is a bond or location susceptible to cleavage by a cleaving agent such as a chemical, an enzyme (e.g., nuclease, dicer, DNAase and RNAase), radiation, temperature, etc. In some embodiments, the cleaving agent is a sequence specific cleaving agent in that it selectively cleaves nucleic acid molecules at a particular site or sequence.

In some embodiments, at least one nucleic acid molecules in a core contains at least one cleavage site susceptible to cleavage after delivery or localization of a particle as described herein to a target site of interest. In some embodiment, nucleic acid molecule(s) in a core have a plurality of cleavage sites and/or are otherwise arranged and constructed so that multiple copies of a particular nucleic acid of interest are released at the target site, upon delivery of a particle as described herein.

In some embodiments, nucleic acid molecule(s) within a core have a self-assembled structure and/or are characterized by an ability to self-assemble in that it/they fold(s) into a stable three-dimensional structure, typically including one or more non-covalent interactions that occur between or among different moieties within the nucleic acid, without requiring assistance of non-nucleic acid entities. In some embodiments, nucleic acid molecule(s) within a core are arranged in a crystalline structure comprising lamellar sheets. In some embodiments, a core comprises or consists of one or more entangled nucleic acid molecules.

In some embodiments, nucleic acid molecule(s) in a core have a molecular weight greater than about $1 \times 10^{10}$ g/mol, about $1 \times 10^9$ g/mol, about $1 \times 10^8$ g/mol, about $1 \times 10^7$ g/mol, about $1 \times 10^6$ g/mol, or about $1 \times 10^5$ g/mol.

As described herein, in some embodiments, nucleic acid molecule(s) in a core includes multiple copies of at least one sequence element (e.g., concatenated in one or more long nucleic acid molecules whose sequence comprises or consists of multiple copies of the sequence element, and/or as discrete nucleic acid molecules each of which has a sequence that comprises or consists of the element, or a combination of both) whose length is within the range between a lower length of at least 5, 10, 15, 20, 25, 30, 35, 40, 45, or more and an upper length of not more than 10000, 9000, 8000, 7000, 6000, 5000, 4000, 3000, 2000, 1000, 900, 800, 700, 600, 500, 400, 300, 200, 100, 90, 80, 70, 60, 50, 40, 30 or less, wherein the upper length is greater than the lower length.

Particles described herein are characterized by a high loading of nucleic acids. In some embodiments, a particle core comprises at least about $1 \times 10^3$, about $1 \times 10^4$, about $1 \times 10^5$, about $1 \times 10^6$, about $1 \times 10^7$, about $1 \times 10^8$, about $1 \times 10^9$, or about $1 \times 10^{10}$ copies of a particular sequence element of interests. In some embodiments, a particle core comprises copies of a particular sequence element of interests in a range of about $1 \times 10^3$ to about $1 \times 10^4$, about $1 \times 10^4$ to about $1 \times 10^5$, about $1 \times 10^5$ to about $1 \times 10^6$, about $1 \times 10^6$ to about $1 \times 10^7$, about $1 \times 10^7$ to about $1 \times 10^8$, about $1 \times 10^8$ to about $1 \times 10^9$, or about $1 \times 10^9$ to about $1 \times 10^{10}$. In some embodiments, a particle core comprises copies of a particular sequence element of interests in a range of about $1 \times 10^3$ to about $1 \times 10^{10}$, about $1 \times 10^4$ to about $1 \times 10^8$ or about $1 \times 10^5$ to about $1 \times 10^7$. In some embodiments, a particle core comprises copies of a particular sequence element of interests in a range of any two values above.

Nucleic acid molecules can carry positive or negative charges. Alternatively, they can be neutral. In some embodiments, a nucleic acid-containing particle core may have a positive or negative surface charge.

In some embodiments, nucleic acid molecules for use in a nucleic acid core as described herein comprise or consist of deoxyribonucleic acid (DNA), ribonucleic acid (RNA), peptide nucleic acid (PNA), morpholino and locked nucleic acid (LNA), glycol nucleic acid (GNA) and/or threose nucleic acid (TNA).

In some embodiments, utilized nucleic acid molecules comprise or consist of one or more oliogonucleotides (ODN), DNA aptamers, DNAzymes, siRNAs, shRNAs, RNA aptamers RNAzymes, miRNAs or combination thereof.

In some embodiments, nucleic acid molecules for use in accordance with the present invention have nucleotide sequence(s) that include(s) one or more coding sequences; one or more non-coding sequences, and/or combinations thereof.

In some embodiments, a coding sequence includes a gene sequence encoding a protein. Exemplary proteins include, but are not limited to brain derived neurotrophic factor (BDNF), glial derived neurotrophic factor (GDNF), neurotrophic factor 3 (NT3), fibroblast growth factor (FGF), transforming growth factor (TGF), platelet transforming growth factor, milk growth factor, endothelial growth factors (EGF), endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-1BBR), TRAIL (TNF-related apoptosis inducing ligand), artemin (GFRalpha3-RET ligand), BCA-1 (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, megakaryocyte derived growth factor (MGDF), keratinocyte growth factor (KGF), thrombopoietin, platelet-derived growth factor (PGDF), megakaryocyte derived growth factor (MGDF), keratinocyte growth factor (KGF), platelet-derived growth factor (PGDF), bone morphogenetic protein 2 (BMP2), BRAK, C-10, Cardiotrophin 1 (CT1), other chemokines, interleukins and combinations thereof.

Coating Films

Particles provided by the present invention may include a coating film on a nucleic acid-containing core. In some embodiments, a film substantially covers at least one surface of a particle core. In some embodiments, a film substantially encapsulates a core.

A film can have an average thickness in various ranges. In some embodiments, an averaged thickness is about or less than 200 nm, 100 nm, 50 nm, 40 nm, 30 nm, 20 nm, 15 nm, 10 nm, 5 nm, 1 nm, 0.5 nm, or 0.1 nm. In some embodiments, an averaged thickness is in a range from about 0.1 nm to about 100 nm, about 0.5 nm to about 50 nm, or about 5 nm to about 20 nm. In some embodiments, an averaged thickness is in a range of any two values above.

In some embodiments, a coating film include one or more layers. A plurality of layers each can respectively contain one or more materials. According to various embodiments of the present disclosure, a layer can consist of or comprise metal (e.g., gold, silver, and the like), semi-metal or non-metal, and metal/semi-metal/non-metal oxides such as silica ($SiO_2$). In certain embodiments, a layer can consist of or comprise a magnetic material (e.g., iron oxide).

Additionally or alternatively, materials of a layer can be polymers. For example, a layer can be polyethyleneimine as demonstrated in Example 1. In some embodiments, a layer is or includes one or more polymers, particularly polymers that which have been approved for use in humans by the U.S. Food and Drug Administration (FDA) under 21 C.F.R. §177.2600, including, but not limited to, polyesters (e.g. polylactic acid, poly(lactic-co-glycolic acid), polycaprolactone, polyvalerolactone, poly(1,3-dioxan-2-one)); polyanhydrides (e.g. poly(sebacic anhydride)); polyethers (e.g., polyethylene glycol); polyurethanes; polymethacrylates; polyacrylates; polycyanoacrylates; copolymers of PEG and poly(ethylene oxide) (PEO). In some embodiments, a polymer is a lipid.

In some embodiments, a layer is or includes at least a degradable material. Such a degradable material can be hydrolytically degradable, biodegradable, thermally degradable, enzymatically degradable, and/or photolytically degradable polyelectrolytes. In some embodiments, degradation may enable release of one or more agents associated with a particle described herein.

Degradable polymers known in the art, include, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine (e.g., poly(L-lysine) (PLL)), poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly(beta-amino esters), which may be suitable for use in accordance with the present application.

In some embodiments, layer-by-layer (LBL) films can be used alternatively or in addition to other layers to coat a particle core in accordance with the present invention. A LBL film may have any of a variety of film architectures (e.g., numbers of layers, thickness of individual layers, identity of materials within films, nature of surface chemistry, presence and/or degree of incorporated materials, etc), as appropriate to the design and application of a coated particle core as described herein. In certain embodiments, a LBL film may has a single layer.

LBL films may be comprised of multilayer units in which alternating layers have opposite charges, such as alternating anionic and cationic layers. Alternatively or additionally, LBL films for use in accordance with the present invention may be comprised of (or include one or more) multilayer units in which adjacent layers are associated via other non-covalent interactions. Exemplary non-covalent interactions include, but are not limited to ionic interactions, hydrogen bonding interactions, affinity interactions, metal coordination, physical adsorption, host-guest interactions, hydrophobic interactions, pi stacking interactions, van der Waals interactions, magnetic interactions, dipole-dipole interactions and combinations thereof. Detailed description of LBL films can be found in U.S. Pat. No. 7,112,361, the contents of which are incorporated herein by reference. Features of the compositions and methods described in the patent may be applied in various combinations in the embodiments described herein.

In some embodiments, a layer can have or be modified to have one or more functional groups. Apart from changing the surface charge by introducing or modifying surface functionality, functional groups (within or on the surface of a layer) can be used for association with any agents (e.g., detectable agents, targeting agents, or PEG).

Agents

In some embodiments, the present invention provides compositions that comprise one or more agents. In some embodiments, one or more agents are associated independently with a core, a film coating the core, or both. For example, agents can be covalently linked to or hybridized to a nucleic acid-containing core, and/or encapsulated in a coating film of a particle described herein. In certain embodiments, an agent can be associated with one or more individual layers of an LBL film that is coated on a core, affording the opportunity for exquisite control of loading and/or release from the film.

In theory, any agents including, for example, therapeutic agents (e.g. antibiotics, NSAIDs, glaucoma medications, angiogenesis inhibitors, neuroprotective agents), cytotoxic agents, diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be associated with the LBL film disclosed herein to be released.

In some embodiments, compositions described herein include one or more therapeutic agents. Exemplary agents include, but are not limited to, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof. In some embodiments, a therapeutic agent to be delivered is an agent useful in combating inflammation and/or infection.

In some embodiments, a therapeutic agent is or comprises a small molecule and/or organic compound with pharmaceutical activity. In some embodiments, a therapeutic agent is a clinically-used drug. In some embodiments, a therapeutic agent is or comprises an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

In some embodiments, a therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof.

An antibiotic used in accordance with the present disclosure may be bacteriocidial or bacteriostatic. Other antimicrobial agents may also be used in accordance with the present disclosure. For example, anti-viral agents, anti-protazoal agents, anti-parasitic agents, etc. may be of use.

In some embodiments, a therapeutic agent may be or comprise an anti-inflammatory agent. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

Those skilled in the art will recognize that this is an exemplary, not comprehensive, list of agents that can be released using compositions and methods in accordance with the present disclosure. In addition to a therapeutic agent or alternatively, various other agents may be associated with a coated device in accordance with the present disclosure.

Methods and Uses

The present invention among other things provide methods of making and using particles described herein. In some embodiments, nucleic acid molecules as described may self-assemble into a core. Optionally, such a core can be coated with a film, wherein the core is characterized by being converted from a first configuration to a second configuration upon coating.

Those of ordinary skill in the art will appreciate that nucleic acid molecules for use in particle cores in accordance with the present invention may be prepared by any available technology. In some aspects, the present invention encompasses the recognition that rolling circle amplification (RCA) and/or rolling circle transcription (RCT) can be a particularly useful methodology for production of nucleic acid molecules for use herein. Exemplary RCA strategies include, for example, single-primer initiated RCA and by various two-primer amplification methods such as ramification amplification (RAM), hyperbranched RCA, cascade RCA, and exponential RCA. In certain embodiments, RNA-containing molecules can be produced via rolling circle transcription (RCT).

The present invention specifically encompasses the recognition that RCA/RCT may be particularly useful for production of long nucleic acid molecules, and/or furthermore may generate nucleic acid molecules. Those skilled in the art will appreciate that a nucleic acid molecule produced by RCA/RCT will typically have a nucleotide sequence comprising or consisting of multiple copies of the complement of the circular template being amplified.

In some embodiments, a template used for RCA/RCT as described herein is or comprises deoxyribonucleic acid (DNA), ribonucleic acid (RNA), peptide nucleic acid (PNA), morpholino and locked nucleic acid (LNA), glycol nucleic acid (GNA) and/or threose nucleic acid (TNA).

In some embodiments, a template used for RCA/RCT as described herein has a nucleotide sequence that includes one or more coding sequences, one or more non-coding sequences, and/or combinations thereof.

In some particular embodiments of RCA/RCT contemplated herein, a polymerase selected from the group consisting of φ29 DNA polymerase and T7 is utilized to perform the RCA/RCT (see, for example, Example 1).

More details of RCA can be found in US Patent Application No. 2010/0189794, the contents of which are incorporated herein by reference. Features of the compositions and methods described in the application may be applied in various combinations in the embodiments described herein. In some embodiments, a first single-stranded nucleic acid molecule is formed by RCA. In some embodiments, the first single-stranded nucleic acid molecule is formed with the aid of a first primer and a nucleic acid polymerase. In some embodiments, a second single-stranded nucleic acid molecule is formed by amplifying the first single-stranded nucleic acid with the aid of a second primer and a polymerase. In some embodiments, a third single-stranded nucleic acid molecule is formed by amplifying the second single-stranded nucleic acid molecule with the aid of a third primer and a polymerase.

A RCA can be repeated with as many primers as desired, e.g., 4, 5, 6, 7, 8, 9, 10 or more primers can be used. In some embodiments, a plurality of primers can be added to templates to form nucleic acid molecules, wherein the plurality can comprise at least about 2, 3, 4, 5, 6, 7, 8, 9, 10, 15, 20, 25, 30, 35, 40, 45, 50, 55, 60, 65, 70, 75, 80, 85, 90, 95, or 100 primers. In some embodiments, more than 100 primers are used. In some embodiments, random fragments of short nucleic acid fragments, e.g., comprising digested or otherwise degraded DNAs, are used as non-specific primers to prime the formation of nucleic acid molecules using rolling circle amplification. As described herein and will be appreciated by those of skill in the art, polymerization reaction conditions can be adjusted as desired to form nucleic acid molecules and self-assembled particles. For example, reaction conditions that favor stringent nucleic acid hybridization, e.g., high temperature, can be used to favor more specific primer binding during amplification.

In some aspects, the present invention specifically encompasses the recognition that LBL assembly may be particularly useful for coating a particle core described herein. There are several advantages to coat particle cores using LBL assembly techniques including mild aqueous processing conditions (which may allow preservation of biomolecule function); nanometer-scale conformal coating of surfaces; and the flexibility to coat objects of any size, shape or surface chemistry, leading to versatility in design options. According to the present disclosure, one or more LBL films can be assembled and/or deposited on a core to convert it to a condensed configuration with a smaller size. In some embodiments, a coated core having one or more agents for delivery associated with the LBL film, such that decomposition of layers of the LBL films results in release of the agents. In some embodiments, assembly of an LBL film may involve one or a series of dip coating steps in which a core is dipped in coating solutions. Additionally or alternatively, it will be appreciated that film assembly may also be achieved by spray coating, dip coating, brush coating, roll coating, spin casting, or combinations of any of these techniques.

In some embodiments, particles described herein including nucleic acid-containing core can be subjected to a cleavage agent, so that nucleic acid molecules are cleaved into multiple copies of a particular nucleic acid of interest and such copies can be released.

In some embodiments, at least one nucleic acid in a nucleic acid core contains at least one cleavage site. In some embodiments, a cleavage site is a bond or location susceptible to cleavage by a cleaving agent such as a chemical, an enzyme, radiation, temperature, etc. In some embodiments, the cleaving agent is a sequence specific cleaving agent in that it selectively cleaves nucleic acid molecules at a particular site or sequence.

In some embodiments, at least one nucleic acid in a nucleic acid core contains at least one cleavage site susceptible to cleavage after delivery or localization of a particle as described herein to a target site of interest. In some embodiment, nucleic acid(s) in a core have a plurality of cleavage sites and/or are otherwise arranged and constructed so that multiple copies of a particular nucleic acid of interest are released at the target site, upon delivery of a particle as described herein.

In some embodiments, particles are provided with a nucleic acid core that comprises one or more sequence elements that targets a particular disease, disorder, or condition of interest (e.g., cancer, infection, etc). For example, provided particles and methods can be useful for dysregulation of genes.

In some embodiments, particles are provided with a nucleic acid core that comprises a plurality of different sequence elements, for example targeting the same disease, disorder or condition of interest. To give but one example, in some embodiments, particles are provided with a nucleic acid core that comprises a plurality of sequence elements, each of which targets a different cancer pathway, for example, as an siRNA that inhibits expression of a protein whose activity contributes to or supports the pathway.

The present invention encompasses the recognition that particles can be designed and/or prepared to simultaneously deliver to a target site (e.g., to a cancer cell) a plurality of different nucleic acid agents (e.g., siRNAs), each of which is directed to a different specific molecular target of interest (e.g., an mRNA encoding a cancer-related protein). The present invention further encompasses the recognition that the described technology permits facile and close control of relative amounts of such different nucleic acid agents that are or can be delivered (e.g., substantially simultaneously) to the site. To give but one example, RCA/RCT templates can be designed and/or assembled with desired relative numbers of copies of different sequences of interest (e.g., complementary to different siRNAs of interest), so as to achieve precise control over the stoichiometry of delivered siRNA(s). In some embodiments, such control achieves synergistic effects (e.g., with respect to inhibiting tumor growth).

In some embodiments, provided particles are administered or implanted using methods known in the art, including invasive, surgical, minimally invasive and non-surgical procedures, depending on the subject, target sites, and agent(s) to be delivered. Particles described herein can be delivered to a cell, tissue, organ of a subject. Examples of target sites include but are not limited to the eye, pancreas, kidney, liver, stomach, muscle, heart, lungs, lymphatic system, thyroid gland, pituitary gland, ovaries, prostate, skin, endocrine glands, ear, breast, urinary tract, brain or any other site in a subject.

EXEMPLIFICATION

Example 1

In this Example, an impactful approach is demonstrated to use the DNA/RNA machinery provided by nature to generate RNAi in polymeric form, and in a manner that actually assembles into its own compact delivery cargo system. Thus, the RNAi is generated in stable form with multiple copy numbers at low cost, and distributed in a form that can readily be adapted for systemic or targeted delivery.

In vitro rolling circle transcription by T7 RNA polymerase to create RNA microsponges Ligased circular DNA templates (0.3 µM) were incubated with T7 RNA polymerase (5 units/µL) at 37° C. for 20 hours in the reaction buffer (8 mM Tris-HCl, 0.4 mM spermidine, 1.2 mM $MgCl_2$, and 2 mM dithiothreitol) including 2 mM rNTP in final concentration. For fluorescently labeling RNA particle, Cyanine 5-dUTP (0.5 mM) was added. The resultant solution was pipetted several times and then sonicated for 5 min to break possible connection of the particles. The solution was centrifuged at 6000 rpm for 6 min to remove the supernatant. Then, RNase free water was added to wash the particles. The solution was sonicated again for 1 min then centrifuged. Repeat this washing step 3 more times to remove the reagents of RCT. Measurement of RNA microsponge concentration was conducted by measuring fluorescence using Quant-iT RNA BR assay kits (Invitrogen). 10 µl of RNA microsponge solution or standard solution was incubated with 190 µl of working solution for 10 min at room temperature. The fluorescence was measured at 630/660 nm by Fluorolog-3 spectrofluorometer (Horiba Jobin Yvon).

Treatment of RNAi Microsponges with Recombinant Dicer

RNAi microsponges were digested with from 1 unit to 1.5 unit recombinant Dicer (Genlantis, San Diego, Calif.) in 12 μl of reaction solution (1 mM ATP, 5 mM MgCl2, 40% (v/v) Dicer reaction buffer). The samples treated for different reaction time from 12 h to 48 h were collected and were then inhibited by adding Dicer stop solution (Genlantis, San Diego, Calif.).

Degradation Experiments of RNAi Microsponges

RNA microsponges were incubated for 24 hrs in 10% of serum at 37° C. Degradation experiments with various concentrations of RNase were also performed for 24 hrs at 37° C. (NEB, Ipswich, Mass.).

Characterization of RNAi Microsponges

JEOL JSM-6060 and JSM-6070 scanning electron microscopes were used to obtain high resolution digital images of the RNA microsponges. The sample was coated with Au/Pd. JEOL 2000FX transmission electron microscope was used to obtain the internal structure of the RNA particle. Zeiss AxioSkop 2 MAT fluorescent microscope was used to image green fluorescently stained RNA microsponges by SYBR II. For characterization of crystalline structure of RNA microsponge, laboratory X-ray powder diffraction (XRD) patterns were recorded using a PANalytical X'Pert Pro diffractometer, fitted with a solid state X'Celerator detector. The diffractometer uses Cu Kα radiation ($\lambda(K\alpha_1)$=1.5406 Å, $\lambda(K\alpha_2)$=1.5433 Å, weighted average $\lambda$=1.5418 Å) and operates in Bragg geometry. The data were collected from 5° to 40° at a scan rate of 0.1°/min.

Assembly of PEI Layer on RNAi Microsponges

For assembly of outer layer, RNA microsponges were mixed with PEI solution, used at a final concentration of up to 5.0 mg/ml. Free PEI was easily removed by centrifugation at 13,700 rpm for 30 min. Repeat this step 2 more times. The PEI layered RNA particles were resuspended in PBS solution (pH 7.4) or MilliQ water.

In vitro siRNA Knockdown Experiments

T22 cells were maintained in growth media comprised of Minimum Essential Media-Alpha Modification (MEM) supplemented with 10% fetal bovine serum (FBS) and 1% Penicillin-Streptomycin. 3 days prior to knockdown experiments, cells were seeded in 6-well plates at 30,000 cells per well. 2 days prior to transfection, each well was co-transfected with 3.5 g each of pRL-CMV and gWIZ-Luc using Fugene-HD according the manufacturer's instructions. 1 day prior to transfection, cells were trypsinized and re-seeded in 96-well plates at an initial seeding density of 2000 cells/well. Cells were allowed to attach and proliferate for 24 hours. All knockdown experiments were performed in triplicate. 50 μL of fluorescently labeled RNAi-MS and RNAi-MS/PEI were added to 250 μL phenol-free Opti-MEM at the final concentration of up to 21.2 fM. Lipofectamine/siRNA complexes were formed at a 4:1 ratio (v/w). Growth media was removed and Opti-MEM was added to cells, followed by RNAi-microsponges or complexes in PBS, for a total volume of 150 μL per well, with no less than 100 μL Opti-MEM per well. Cells were incubated with siRNA constructs for 4 hours, after which media was removed and replaced with 10% serum-containing growth medium. A Luciferase assay was performed as using the Dual-Glo Luciferase Assay Kit (Promega, Madison, Wis.) and measured on a Perkin Elmer Plate 1420 Multilabel Counter plate reader. GFP expression was measured after quenching of the luciferase signal with the Stop-and-Glo reagent from Promega.

In vivo siRNA Knockdown Experiments

T22-Luc is a genetically defined mouse ovarian cancer cell line (p53–/–, Akt, myc) that stably expresses luciferase after infection with pMSCV-puro-Firefly luciferase viral supernatant and selecting the cells in a medium containing 2.0 ig/ml of puromycin for 1 week. T22-Luc tumors were induced on both hind flanks of female nude mice (5 weeks old) with a single injection of 2-5 million cells in 0.1 mL media. After the tumors grew to ~100 $mm^3$ in volume, intratumoral injections of RNAi-microsponges were given in volumes of 50 uL. To determine the degree of luciferase knockdown, D-Luciferin (Xenogen) was given via intraveneously (tail vein injection, 25 mg/kg) and bioluminescence images were collected on a Xenogen IVIS Spectrum Imaging System (Xenogen, Alameda, Calif.) 10 minutes after injection. Living Image software Version 3.0 (Xenogen) was used to acquire and quantitate the bioluminescence imaging data sets.

Chemicals and DNA Sequences: T7 RNA polymerase and Ribonucleotide Solution Mix were purchased from New England Biolabs (Beverly, Mass.) in pure form at a concentration of 50,000 units/ml and 80 mM, respectively. RNase Inhibitor (RNAsin Plus) was purchased from Promega (Madison, Wis.) at a concentration of 40 units/μl. Linear 25,000 g/mol (Mw) polyethyleneimine (PEI) was purchased from Polysciences Inc. (Warrington, Pa.). Other chemical reagents were purchased from Sigma Aldrich (St. Louis, Mo.). Oligonucleotides were commercially synthesized and PAGE purified (Integrated DNA Technologies, Coralville, Iowa). Sequences of the oligonucleotides are listed in Table 1. siRNA for control experiments was purchased from Dharmacon RNAi Technologies. Dual-Glo Luciferase Assay System was purchased from Promega (Madison, Wis.). All other cell culture reagents were purchased from Invitrogen. GFP- and Luciferase-expressing T22 cells were a gift of the laboratory of Phil Sharp (MIT). Vivo Tag 645 and Cyanine 5-dUTP was purchased from Visen/PerkinElmer.

TABLE 1

Oligonucleotide sequences of linear ssDNA and T7 promoter.

| Strand | Sequence |
|---|---|
| Linear ssDNA | 5'-Phosphate-ATAGTGAGTCGTATTAACGTACCAACAACTTACGCTG AGTACTTCGATTACTTGAATCGAAGTACTCAGCGTAAGTTTAGAGGCATAT CCCT-3' (SEQ ID NO: 1) |
| Promoter | 5'-TAATACGACTCACTATAGGGAT-3' (SEQ ID NO: 2) |

Linear ssDNA

```
                    Complementary to sense siRNA
                              ⌒
              ⌒                         ⌒
Complementary to T7 Promoter
                    Complementary to antisense siRNA
```

Circularization of Linear DNA: 0.5 µM of phosphorylated linear ssDNA (ATAGTGAGTCGTATTAACGTAC-CAACAACTTACGCTGAGTACTTCGATTACTTGAAT CGAAGTACTCAGCGTAAGTTTAGAGGCATATCCCT) (SEQ ID NO: 1) was hybridized with equimolar amounts of short DNA strands containing the T7 promoter sequence (TAATACGACTCACTATAGGGAT) (SEQ ID NO: 2) by heating at 95° C. for 2 min and slowly cooling to 25° C. over 1 hour. The circular DNA is synthesized by hybridizing a 22 base T7 promoter with a 92 base oligonucleotide which has one larger (16 bases) and one shorter (6 bases) complementary sequence to the T7 promoter (Table 1). The nick in the circular DNA was chemically closed by T4 DNA ligase (Promega, Madison, Wis.), following commercial protocol.

Gel Electrophoresis: The resultant solution after dicer treatment of the RNA microsponges was run in a 3% agarose ready gel (Bio-Rad) at 100 V at 25° C. in Tris-acetate-EDTA (TAE) buffer (40 mM Tris, 20 mM acetic acid and 1 mM EDTA, pH 8.0, Bio-Rad) for 90 min. The gel was then stained with 0.5 mg/ml of ethidium bromide in TAE buffer. The gel electrophoresis image was used to calculate the number of siRNA from RNA particle. By comparing the band intensity of cleaved 21 bp RNA strands to standard RNA strands, the amount of siRNA, which was converted from RNAi microsponges, was calculated (Table 2). Although up to 460 ng of siRNA can be theoretically obtained from 1 µg of RNAi microsponges, the particles were experimentally converted to 94.5 ng of siRNA by Dicer treatment under optimal conditions.

TABLE 2

Peak positions and d-spadings for RNAi-microsponge

| Peak position, q [Å$^{-1}$] | Spacing d [Å] |
|---|---|
| 0.57 | 11.00 |
| 1.18 | 5.32 |
| 1.77 | 3.56 |
| 2.16 | 2.91 |
| 1.04 | 6.02 |
| 2.08 | 3.03 |

Spacing was determined by Bragg's Law.

$$d = n\lambda/2 \sin\theta$$

Also, the scattering vector q was determined from the following equation.

$$q = 4\pi \sin\theta/\lambda$$

To determine the thickness of crystallite was determined from Scherrer's Formula.

$$D = 2\pi K/\Delta q$$

Here, K=0.9 is the Scherrer constant, and $\Delta q$ is the radial full width at half maximum of a given Bragg spot. D is thickness of crystallite. $\lambda$ is the wavelength of the x-ray radiation (here, $\lambda$ is 1.54).

| FWHM, $\Delta q$ [Å$^{-1}$] | Thickness of Crystallite, D [Å] |
|---|---|
| 0.077 | 73.3 |

Figure 6:
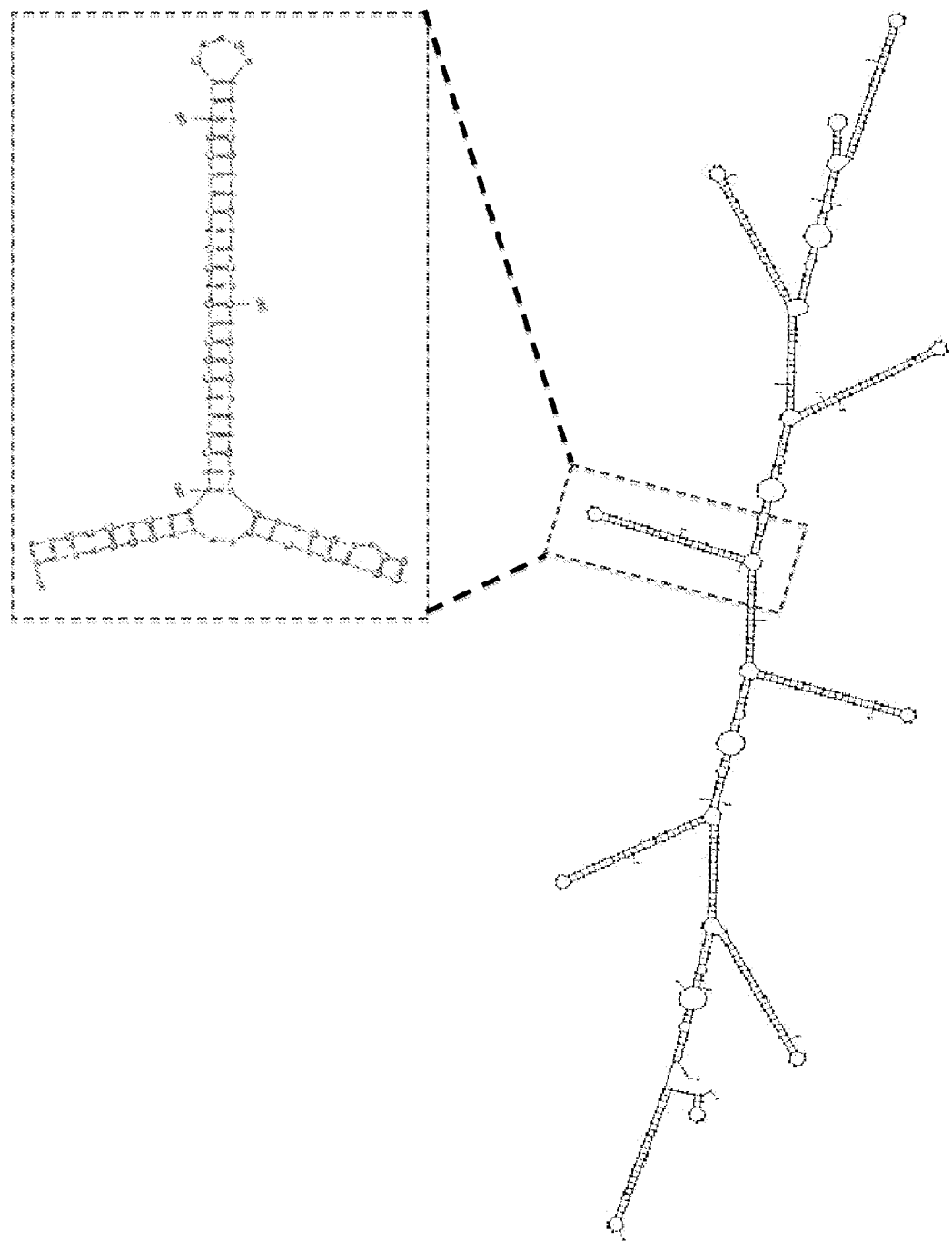
FIG. 6. Secondary structure of eight repeated units produced by RCT (using M-fold software). Figure discloses full-length sequence as SEQ ID NO: 3. Figure also discloses nucleotides 191-259 and 542-560 of SEQ ID NO: 3.

Here, the crystallite thickness is estimated to be ~7.4 nm as determined from the Scherrer equation. The 7.4 nm is close to the theoretical length of double stranded 21 bp siRNA by considering that one base pair corresponds to 2.6-2.9 Å of length along the strand (21×2.6-2.9=54.6-60.9 Å). Considering that the polymer might fold according to the structure displayed FIG. 6, the observed thickness might correspond to the length of a double stranded 21 bp siRNA coupled to the width of a duplexed RNA helix of approximately 20 Å [Nucleic Acids Research, 27, 949-955 (1999)]. This would theoretically amount to 74.6 to 80.9 Å. In addition, the rest of RNA strands could be easily packing to form ordered structure since the persistence length of single-stranded RNA is less than 1 nm. However, double stranded RNA part should be rigid because persistence length of double stranded RNA is about 64 nm (Single-Molecule Measurements of the Persistence Length of Double-Stranded RNA, Biophys J. 2005 April; 88(4): 2737-2744).

Dynamic Light Scattering (DLS) and Zeta Potential: The size and surface charge of RNAi microsponges were measured using Zeta PALS and Zeta Potential Analyzer software (Brookhaven Instruments Corp., Holtsville, N.Y.). The RNAi microsponges were diluted in Milli-Q water and all measurement were carried out at 25° C. Three measurements each with 10 sub-runs were performed for each sample. Molecular weight of RNA microsponges, 1.36×10$^{10}$ g/mole, was obtained from Zeta PALS software.

Calculation of Amount of siRNA Generated from RNAi Microsponges: From the measured molecular weight of the RNA microsponges, the number of periodically repeated 92 base RNA strands (from 92 base circular DNA templates) in a single RNA microsponge was calculated as follows:

Molecular Weight of 92 base RNA strand=28587 g/mole

Number of 92 base RNA strands (cleavable RNA strands) in one RNA microsponge=1.36×10$^{10}$/28587=4.76×10$^5$ In theory, 480000 of siRNA can be maximally generated from one RNAi microsponge.

Experimentally, the amount of cleaved siRNA from one RNA microsponge was determined using the gel electrophoresis results.

siRNA from one RNA particle=Amount of siRNA from 1 µg of RNA microsponge/amount of 1 µg of RNA microsponge=(0.0945 µg/12600 µg/mol)/(1 µg/1.36×10$^{10}$/mol)=102,000

According to gel electrophoresis results following the Dicer treatment, 102,000 siRNA strands were generated from one RNAi microsponge under optimal conditions. This result shows that 21% of potential RNAi is converted as siRNA. In our hypothesis, some portion of the RNA is not as readily accessed by dicer in a more close-packed self-assembled RNA structure. Therefore, multimers such as dimer, trimer, and tetramer of repeat RNA unit as incomplete dicing products could be produce.

Calculation of Amount of Liposome by Lipofectamine with siRN: The number of liposome can be calculated by the following equation, $$N_{liposome} = N_{lipid}/N_{tot}$$

If 100 nm liposomes are unilamellar structure, the number of lipids in a 100 nm size liposome is about 80047. With 2 mg/ml of Lipofectamine™ reagent (Invitrogen) solution, which is 3:1 (w/w) liposome formulation of DOSPA (2,3-dioleoyloxy-N-[2(sperminecarboxamido)ethyl]-N,N-dimethyl-1-propaniminium trifluoroacetate) and DOPE (dioleoyl-L-a-phosphatidylethanolamine), 1:4 ratio of siRNA/Lipo (w/v) is formed.

Based on our calculation, about 150 times more number of liposomes that are made of lipofectamine agent are needed to deliver same number of siRNA in comparison to microsponges. For example, to deliver 1 nmole of siRNA, 1.5 pmole of liposome is necessary (in case of RNAi-MS, about 10 fmole of RNA-MS can deliver 1 nmole of siRNA). This is an important issue for the cell type that does not easily allow cellular uptake and low off-target/toxicity.

Materials for In Vitro Biological Characterization: The siRNA was purchased from Dharmacon RNAi Technologies. Dual-Glo Luciferase Assay System and Fugene-HD were purchased from Promega. All other cell culture reagents were purchased from Invitrogen. T22 cells stably expressing both GFP and firefly luciferase, untransfected T22 cells, and pRL-CMV (Renilla luciferase) plasmid were a gift of the laboratory of Phil Sharp (MIT). gWIZ-Luc (Firefly luciferase) plasmid was obtained from Aldevron. (Firefly) Branched 25,000 g/mol ($M_w$) polyethyleneimine (PEI) and other chemical reagents were purchased from Sigma Aldrich. Vivo Tag 645 was purchased from Visen/PerkinElmer.

Cell Proliferation Assay: T22 cells were seeded at 2000 cells/well in a 96-well clear, flat-bottomed plate and transfected according to the above protocol. Cells were incubated with RNAi-microsponges or RNAi-microsponge/PEI for 4 hours, after which media was removed and replaced with 10% serum-containing growth medium. After 48 hours, each well was treated with 20 μ of MTT reagent (1 mg/mL in MEM) for an additional 4 hours. Media was then removed and formazan crystals were solubilized in 50:50 DMF:water with 5% SDS. After 12 hours, absorbance was read at 570 nm.

Cell Uptake Test by Confocal Microscopy: 8-well Lab-Tek chamber slides (Thermo Fisher, Waltham, Mass.) were treated for 20 min with human fibronectin in PBS at 0.1 mg/mL. The fibronectin was removed and T22 cells were trypsinized and seeded in each well at a concentration of 4000 cells/well 24 h before transfection. 50 μL of fluorescently labeled RNAi-MS and RNAi-MS/PEI were added to 250 μL phenol-free Opti-MEM at the final concentration of up to 21.2 fM. After 4 hours, RNAi-microsponges were removed, cells were fixed with 3.7% formaldehyde in PBS, stained with Hoechst 33342 (Pierce) and Alexa Fluor 488® phalloidin (Invitrogen) and washed 3 times with PBS. Imaging was done on a PerkinElmer Ultraview spinning disc confocal (PerkinElmer, Waltham, Mass.).

Materials for In Vivo siRNA Knockdown Experiments: T22-Luc cells were a generous gift from Dr. Deyin Xing, Professor Philip Sharp (MIT) and Dr. Sandra Orsulic (Cedars-Sinai medical center). Tumors from nude mice injected with Brca1 wild-type cell line C22 were used to generate T22 tumor cell lines (Cancer Res. 2006 Sep. 15; 66(18): 8949-53). T22-Luc is a genetically defined mouse ovarian cancer cell line (p53−/−, Akt, myc) that stably expresses luciferase after infection with pMSCV-puro-Firefly luciferase viral supernatant and selecting the cells in a medium containing 2.0 ìg/ml of puromycin for 1 week.

Figure 8:
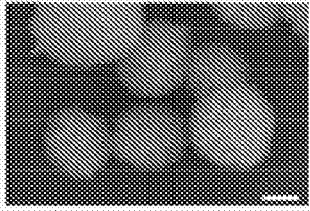
FIG. 8. SEM images of RNAi-microsponges after incubation with various concentrations of RNase (RNase I for single stranded RNA and RNase III for double stranded RNA, NEB, Ipswich, Mass.). The degradation of RNA microsponge at different concentrations of RNase suggests that our microsponge is made of RNA. At lower concentrations, the size of microsponges is decreased but still protected from RNase. As the concentration increase, the microsponges is not able to maintain the particle form by degradation. Finally, RNA fragments of the microsponges are completely disappeared at the higher concentration of RNase. However, RNA microsponge is intact after incubation with high concentration of DNase I, suggesting that circular DNA is not the building material for microsponges. Scale bars indicate 1 μm.
Figure 18:
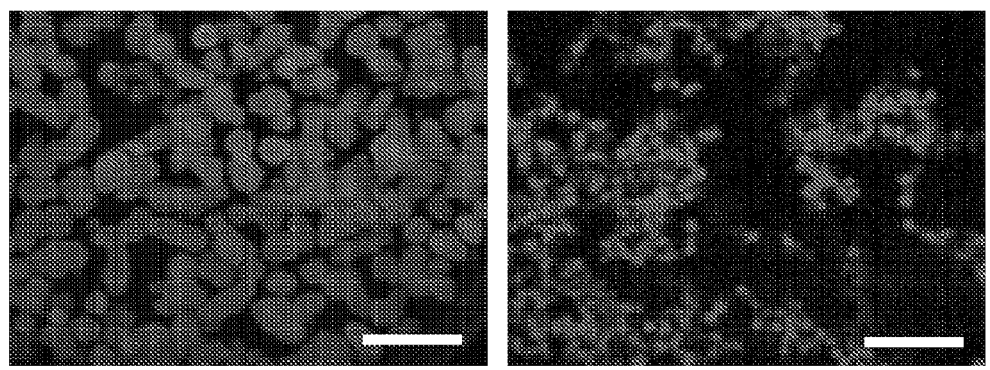
FIG. 18. Fluorescence microscopic images of RNAi-microsponge before (left) after incubating in 10% Serum for one day at 37° C. (right). Scale bar indicates 10 μm. The size of the RNAi-microsponge is reduced, possibly by degradation of RNAse, but still maintain the particle structure, supporting the idea that the RNA in the RNAi-microsponges are protected from degradation within the sponge structure.

Degradation Experiments of RNAi Microsponges: For degradation test, RNA microsponges were incubated for 24 hrs in 10% of serum at 37° C. (FIG. 18). We have also carried out additional experiments with various concentrations of RNase for 24 hrs at 37° C. (FIG. 8) [RNase I (from 0.05 U/μl to 5 U/μl) for single stranded RNA and RNase III (from 0.02 U/μl to 1.2 U/μl) for double stranded RNA, NEB, Ipswich, Mass.]. As a control, RNA microsponges were incubated with 10 U/μl of DNase I (NEB, Ipswich, Mass.) for 24 hrs at 37° C.

By taking advantage of new RNA synthetic methods for the generation of nanostructures via rational design, we utilize an enzymatic RNA polymerization to form condensed RNA structures that contain predetermined sequences for RNA interference by rolling circle transcription (RCT).

Here we design and use RNA polymerase to generate elongated pure RNA strands as polymers that can self-assemble into organized nano- to microstructure, which is key for efficient delivery and high cargo capacity, offering the combined benefit of low off-target effects and low toxicity[4]. Using a new approach, we utilize the T7 promoter as a primer so that extremely high molecular weight RNA strands can be produced. As shown in FIG. 1, long linear single stranded DNA encoding complementary sequences of the antisense and sense sequences of anti-luciferase siRNA are first prepared. Because both ends of the linear DNA are also partially complementary to the T7 promoter sequence, the long strand is hybridized with a short DNA strand containing the T7 promoter sequence to form circular DNA (see Table 1). The nick in the circular DNA is chemically closed with a T4 DNA ligase. The closed circular DNA is then used to produce RNA transcripts via RCT, encoding both antisense and sense sequences of anti-luciferase siRNA yielding hairpin RNA structures (see FIG. 6). The hairpin RNA structures can actively silence genes when converted to siRNA by Dicer. From In vitro RCT of the circular DNA, we can obtain multiple tandem copies of the sequence in coils of single-stranded and double stranded RNA transcripts. Although the products might be compared to DNA toroidal condensates, in this case, there is not a charged condensing element that assists in the formation of structure.

Figure 2:
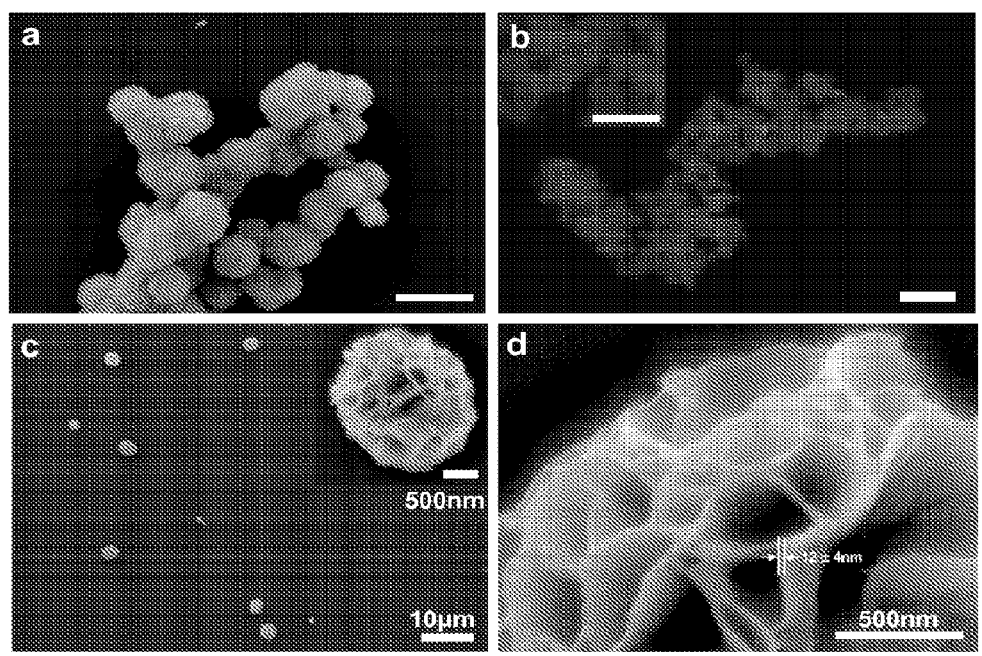
FIG. 2. Characterization of the RNAi-microsponge. a, SEM image of RNAi-microsponge. Scale bar: 5 μm. b, Fluorescence microscope image of RNAi-microsponges after staining with SYBR II, RNA specific dye. Scale bars: 10 μm and 5 μm (Inset). c, d, SEM images of RNAi-microsponges after sonication. Low magnification image of RNAi-microsponges (c). Scale bars: 10 μm and 500 nm (Inset). High magnification image of RNAi-microsponge (d). Scale bar: 500 nm.
Figure 7:
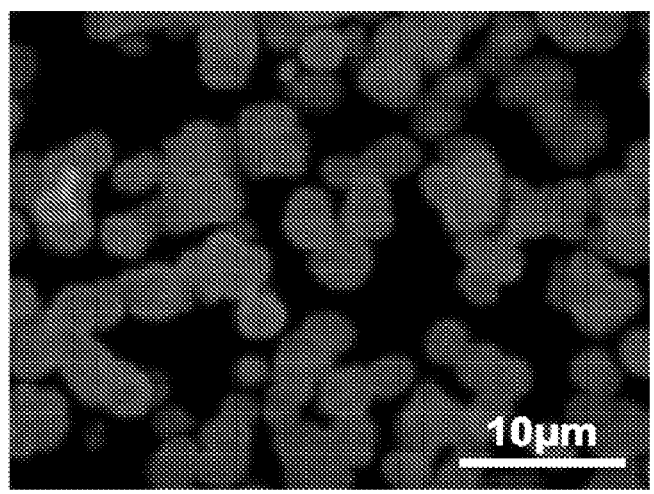
FIG. 7. Confocal image of RNAi-microsponges labeled with Cyanine 5-dUTPs. RNAi polymerization took place with rolling circle transcription in the presence of Cyanine 5-dUTPs used as one of the ribonucleotides to form the RNA-microsponge. The red fluorescence from the RNAi-microsponge confirms that the microsponge is formed of RNA.

The RNA transcripts form porous sponge-like superstructures with nanoscopic structure readily visible in scanning electron microscope (SEM) image (FIG. 2a). Because of the structural similarity, we refer to the resulting RNA product as an RNA interference (RNAi) microsponge. Unlike conventional nucleic acid systems, our RNAi-microsponge exhibits a densely packed molecular scale structure without the use of an additional agent. We confirmed that the RNAi-microsponges are composed of RNA by staining with SYBR II and labeling with Cyanine 5-dUTPs, and observing the resulting bright green and red fluorescence, respectively (FIG. 2b and FIG. 7). Also, we provide additional evidence with an RNase digestion experiment at various concentrations of RNase. The results clearly show the rate-dependent degradation of the RNA microsponge at high concentrations of RNase (see FIG. 8). Mono-disperse RNA microsponges were prepared with short sonication (FIG. 2c). The particles exhibit a uniform size of 2 μm, and consistent nano-pleated or fan-like spherical morphology. Based on the molecular weight and concentration, each RNAi-microsponge contains approximately a half million tandem copies of RNA strands that are cleavable with Dicer. A higher magnification SEM image of the RNA particles reveals that the sponge-like structure is constructed from RNA sheets that are approximately 12±4 nm thick (FIG. 2d).

Figure 3:
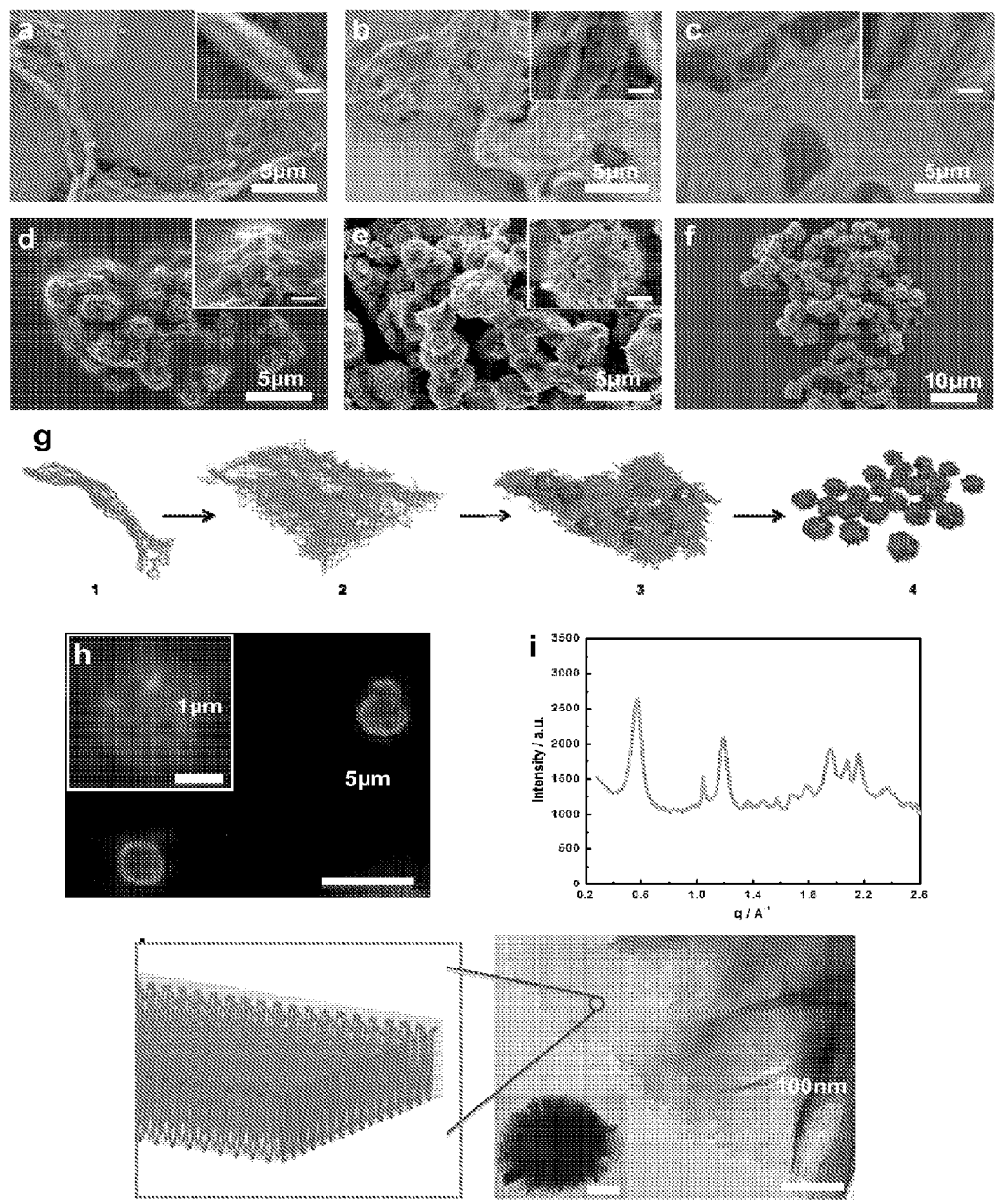
FIG. 3. Formation of sponge-like spherical structures purely with RNA strands. a, b, c, d, and e. SEM images of RNA products of time-dependent RCT at 37° C. for 1 h (a), 4 h (b), 8 h (c), 12 h (d), and 16 h (e). Scale bars: 5 μm and 500 nm (inset). f, Image of mature RNAi microsponges after 20 h RCT. Scale bar: 10 μm. g, Schematic illustration of the formation of RNAi-microsponges. The spherical sponge-like structure is formed through a series of preliminary structures. A tandem copy of RNA strands from the RCT reaction are entangled and twisted into a fiber-like structure1. As the RNA strands grow, they begin to organize into lamellar sheets that gradually become thicker2; as the internal structure of the sheets begin to get very dense, some of the RNA sheets begin to grow in the Z direction, possibly due to limited packing area for the RNA polymer as it is produced by the reaction. This process could generate wrinkled semi-spherical structure on the sheet3. Finally, the entire structure begins to pinch off to form individual particles consisting of gathered RNA sheets4. h, Polarized optical microscopy of RNAi-microsponge. Scale bars: 5 μm and 1 μm (Inset). i, X-ray diffraction pattern of RNAi-microsponge. j, TEM images of RNAi-microsponge and schematic representation of the proposed crystal-like ordered structure of RNA sheet in microsponge. Scale bars: 100 nm and 500 nm (Inset).
Figure 9:
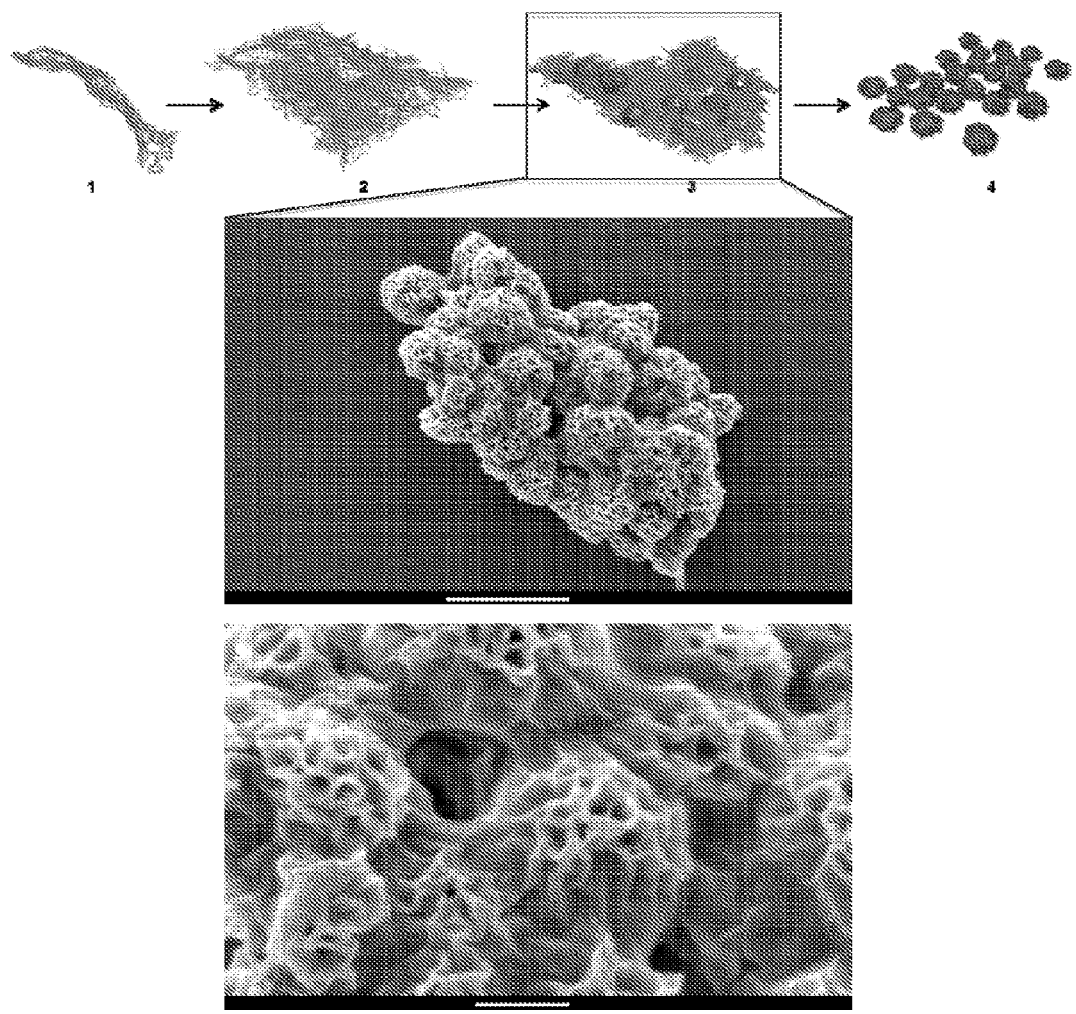
FIG. 9. Cartoon schematic image of the formation of RNAi-microsponges (Top). Scanning electron microscope images of preliminary structure of RNAi-microsponges after 12 h rolling circle transcription (Bottom). Scale bars indicate 5 μm and 1 μm.
Figure 10:
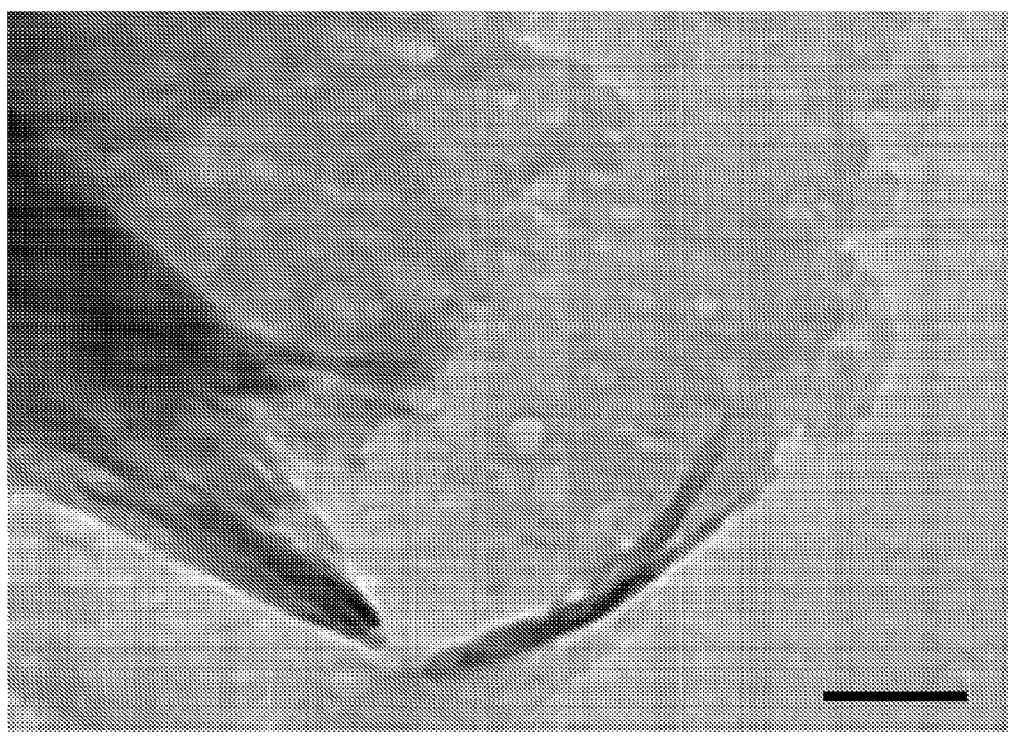
FIG. 10. Transmission electron microscope image of RNAi microsponge. Multi-layered RNA sheets are shown in high magnification image. Scale bar indicates 50 nm.
Figure 11:
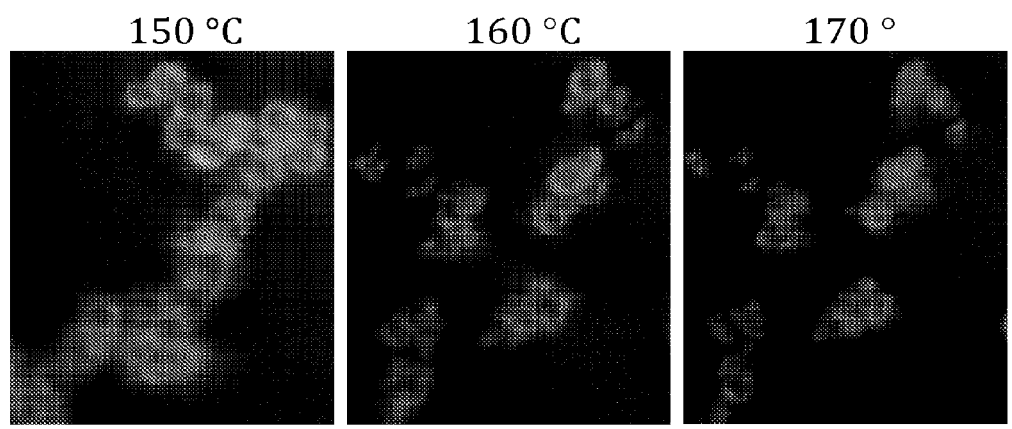
FIG. 11. Polarized optical microscopy images of RNAi-MS with heating stage.
Figure 12:
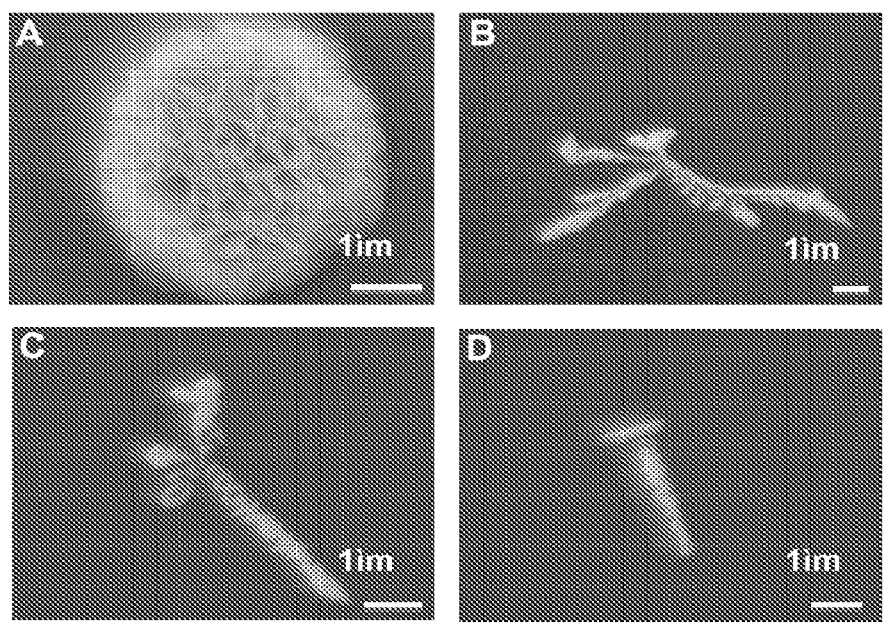
FIG. 12. Scanning electron microscope images of RNA products by rolling circle transcription with different concentrations of circular DNA from 100 nM (A), 30 nM(B), 10 nM(C), and 3 nM(D). With 100 nM of circular DNA, sponge-like structures from RNA products are shown, however, microsponges are not generated with 30 nM, 10 nM, and 3 nM of circular DNA. In figure B-D, RNA products form fiber-like structures that are similar to the products of time-dependent experiment after 1 hour RCT (see FIG. 2A in main text). According to results from time dependent and concentration dependent experiments, we hypothesize that the mechanism of formation of RNAi-microsponge is crystallization of RNA polymers into thin lamellae by nucleation of poly-RNA when its concentration is higher than a critical concentration beyond which individual crystalline forms aggregate and merge into superstructures. Therefore, the final structure is reminiscent of the lamellar spherulite structures that are formed by highly crystalline polymers [Formation of Spherulites in Polyethylene. Nature 194, 542-& (1962)].

To examine the formation of the sponge-like spherical structures from their RNA strand building blocks, time-dependent experiments were performed during the RCT polymerization. The morphologies of the RNA superstructures were revealed by SEM after 1 h, 4 h, 8 h, 12 h, 16 h and 20 h RCT reaction time. As shown in FIG. 3a, the RCT products first form a fiber-like structure in the early stages of the polymerization. After additional reaction time, a sheet-like structure is formed (FIG. 3b). At the 8 h time point, the sheet-like structure became thicker and began to exhibit a densely packed internal structure (FIG. 3c). Wrinkled and semi-spherical structures begin to appear on the sheet structures in the 12 h reaction sample (FIG. 3d and FIG. 9). After 16 h, the morphology of the RNA polymer product transforms into interconnected globular superstructures in which the sheets are re-organized into a complex buckled and folded internal structure (FIG. 3e). These spherical structures start to separate into individual particles, and after 20 h, the final spherical sponge-like structures were observed (FIGS. 3f and 2a). Based on the SEM images from time-dependent experiments, a schematic cartoon of the process of formation of sponge-like superstructure is suggested in FIG. 3g. The final structure is reminiscent of the lamellar spherulite structures that are formed by highly crystalline polymers when nucleated in the bulk state or solution. In the case of traditional synthetic polymers such as polyethylene or polyethylene oxide, the thickness of the lamellar sheets corresponds to the dimensions of chain-folded polymer molecules. It is possible that as the RNA polymer is continuously generated during the RCT reaction, and reaches very high molecular weight at high localized concentrations, a similar ordering and assembly process occurs here. Thus far, such a self-assembled crystalline superstructure has not been observed for RNA polymers. The crystalline structure of RNAi-microsponge was confirmed with polarizing optical microscopy (POM); under crossed polarizers, birefringence of the individual particles is observed (FIG. 3h). In comparison to the SEM image (inset of FIG. 2c), it appears that the RNA sheet has a crystal-like ordered structure (Inset of FIG. 3h). X-ray diffraction further confirmed the crystalline structure of the RNAi-microsponge (FIG. 3i). The crystallite thickness is estimated to be ~7.4 nm as determined from the Scherrer equation (Table 2). This finding is consistent with the thickness from SEM images although the resolution of SEM is not as sensitive at the nanoscale. In addition, transmission electron microscope (TEM) images (FIG. 3j and FIG. 10) showing densely assembled RNA sheet structures in the RNAi-microsponge support the proposed structure, as shown in schematic form in FIG. 3j. Similar to liquid crystal phases from duplex DNA, the high molecular weight of RNA polymers with periodic RNA duplexes leads to the formation of crystal-like ordered structures. The melting experiment using POM with a heating stage show that the RNAi-microsponge is pretty stable up to 150° C. which is much higher than the melting temperature of any double helix DNA or RNA molecules, suggesting that the formation of the RNAi-microsponge is dominantly based on the ordered crystalline structure of RNA polymers (FIG. 11). The assembly of the RNA polymer was also observed when polymerized at different concentrations of the rolling circle DNA polymerizing or initiating units (FIG. 12). At lower concentrations, individual branched dendritic polycrystals were formed in solution, but they did not assemble into microparticles until a critical concentration of DNA was achieved. The concentration dependence, the appearance of more traditional crystalline structures at low concentration, as well as the observed crystallite thickness of 7.4 nm for the sponge layer structures, which corresponds to the length of the rigid 21 bp RNA repeat sequence, were all consistent with phenomena observed for the formation of spherulitic superstructures of chain folded lamellar sheets.

Figure 4:
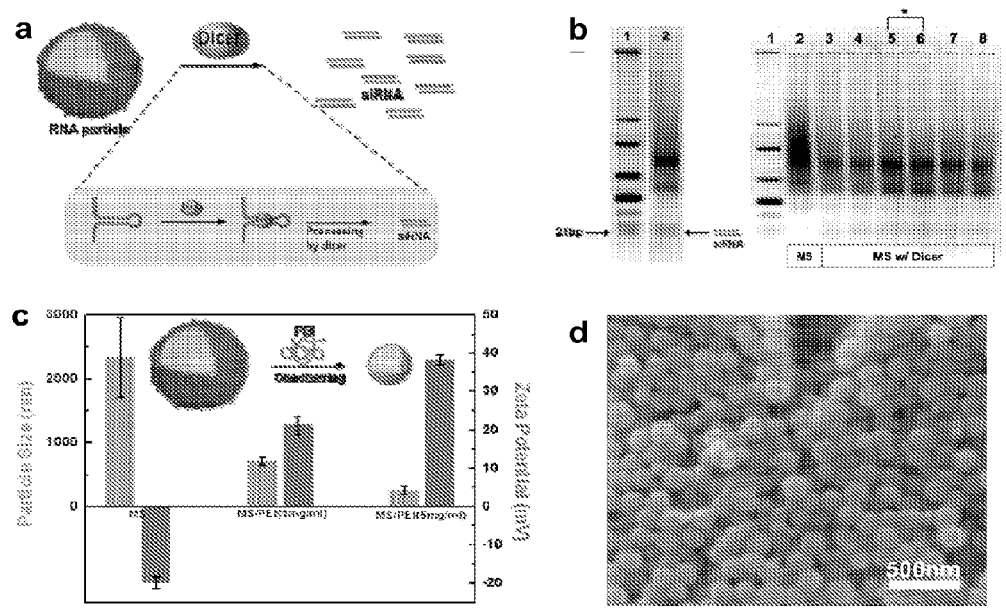
FIG. 4. Generating siRNA from RNAi-microsponge by RNAi pathway and condensing RNAi-microsponge for transfection. a, Schematic illustration of generating siRNA from RNAi-microsponges by Dicer in RNAi pathway. b, Gel electrophoresis result after Dicer reaction. Lane 1 and 2 indicate double stranded RNA ladder and RNAi-microsponges(MS) after treatment with Dicer (1 unit) for 36 hours, respectively (Left). Land 1 and 2 indicate double stranded RNA ladder and RNAi-microsponges without Dicer treatment (Right). Lane 3 to 8 correspond to 12 h, 24 h, 36 h, and 48 h reaction with 1 unit of Dicer and 36 h reaction with 1.25 and 1.5 unit of Dicer, respectively. Increasing the amount of Dicer did not help to generate more siRNA (lane 7 and 8 of FIG. 4b, right). The amount of generated siRNA from RNAi-microsponges was quantified relative to double-stranded RNA standards. 21% of the cleavable double stranded RNA was actually diced to siRNA because Dicer also produced the two or three repeat RNA units that included two or three non-diced RNA duplex. The results suggest the possibility that in a more close-packed self-assembled structure, some portion of the RNA is not as readily accessed by dicer. c, Particle size and zeta potential before and after condensing RNAi-microsponge with PEI. d, SEM image of further condensed RNAi-microsponge with PEI. Scale bar: 500 nm. The size of RNAi-microsponge was significantly reduced by linear PEI because the RNAi-microsponge with high charge density would be more readily complexed with oppositely charged polycations. The porous structure of RNAi-microsponge was disappeared by the condensation.

The RNAi-microsponges have a highly localized concentration of RNA strands, as they essentially consist of near 100% potential RNAi. For this reason, these systems should be an effective means to deliver and generate siRNA through intracellular processing mechanisms. The RNA structures were designed to be cleaved by the enzyme Dicer by cutting double-stranded RNA into approximately 21-nt RNA duplexes in the cytoplasm, where it can be converted to siRNA by the RNA-induced silencing complex (RISC) for gene silencing (FIG. 4a). To confirm Dicer cleavage of RNAi-microsponge, they were incubated with recombinant Dicer and the products were analyzed by gel electrophoresis (FIG. 4b). In the presence of recombinant Dicer, RNAi-microsponges yielded 21 bp products (FIG. 4b, left); whereas there are no RNA strands as small as the 21 bp siRNA without Dicer treatment (lane 2 of FIG. 4b, right). Due to the amount of cleavable RNA strands and size of RNAi-microsponge, recombinant Dicer required at least a 36 h reaction time to generate the maximum amount of siRNA (lane 3 to 8 of FIG. 4b, right). 9.5% (w/w) of RNAi-microsponge was converted to siRNA, indicating 21% of the cleavable double stranded RNA was actually diced to siRNA (Table 3). Dicer also produced the two or three repeat RNA units that included two or three non-diced RNA duplex (FIG. 4b). With these results, we estimate that each individual RNAi-microsponge can yield ~102000 siRNA copies (see Calculation above).

TABLE 3

Amount of cleaved siRNA from 1 µg of RNAi-microsponges from gel electrophoresis results.

| | Intensity (abitrary) | Std. | Amount (ng) | |
|---|---|---|---|---|
| 21 bp of dsRNA Ladder | 159.3 | 16.4 | 93.8 ± 9.7 | Reference |
| siRNA from RNA particles | 160.4 | 8.8 | 94.5 ± 5.2 | |

Figure 13:
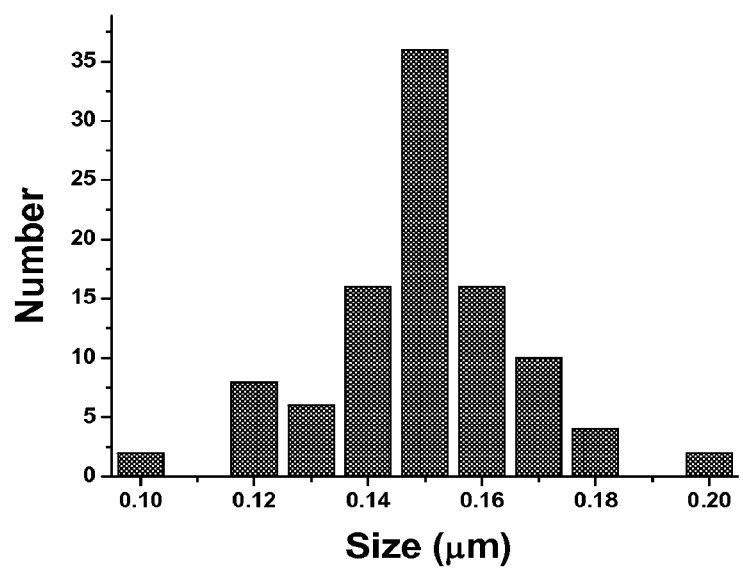
FIG. 13. Distribution of the particle size of RNAi-microsponge/PEI.

To enhance the cellular uptake of the RNA particle, the synthetic polycation, polyethylenimine (PEI) was used to condense the RNAi-microsponge and generate a net positively charged outer layer. Due to the high negative charge density of the RNAi-microsponge, cationic PEI was readily adsorbed onto the particles by electrostatic interaction. The change of particle surface charge (zeta potential) from −20 mV (RNAi-microsponge) to +38 mV (RNAi-microsponge/PEI) indicates the successful assembly of RNAi-microsponge with PEI (FIG. 4c). The size of the particles was significantly decreased to 200 nm from the original average size of approximately 2 µm (FIG. 4c). The shrinking was also confirmed by SEM image, showing approximately 200 nm monodisperse particles (FIG. 4d and FIG. 13). It is worth noting that a single PEI layered RNAi-microsponge still contains the same number of cleavable RNA strands, thus yielding an extremely high siRNA density. To the best of our knowledge, this represents the highest number of siRNA molecular copies encapsulated in a nanoparticle; typically the loading of siRNA can be challenging for standard polymeric carriers.

Figure 5:
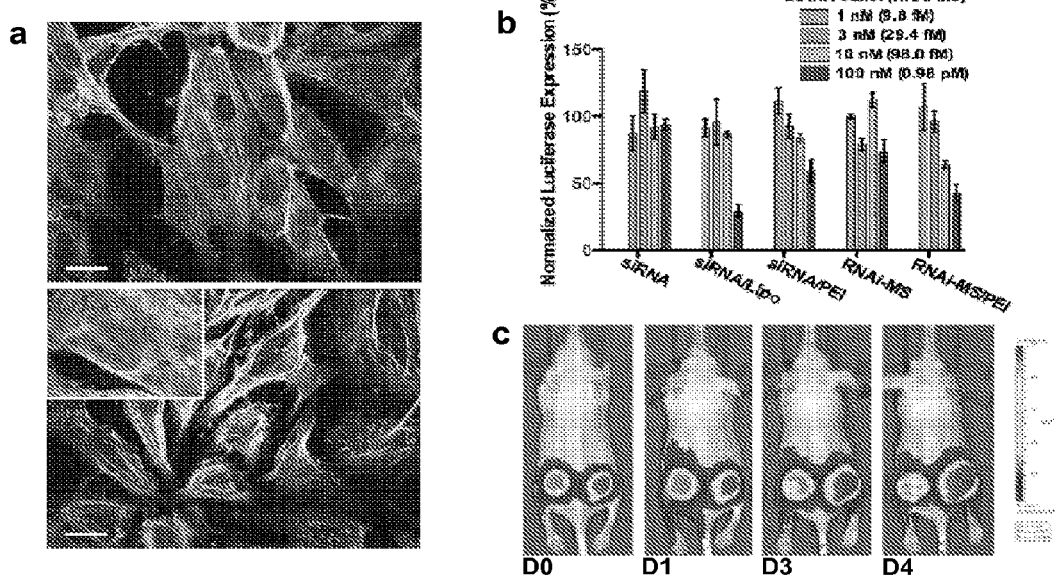
FIG. 5. Transfection and gene-silencing effect. a, Intracellular uptake of red fluorescent dye-labeled RNAi-microsponge without PEI (top) and RNAi-microsponge/PEI (bottom). To confirm the cellular transfection of RNA particles, red fluorescence labeled both particles were incubated with T22 cells. Fluorescence labeled RNAi-microsponge without PEI outer layer showed relatively less cellular uptake by the cancer cell line, T22 cells, suggesting that the larger size and strong net negative surface charge of RNAi-microsponge likely prevents cellular internalization. b, Suppression of luciferase expression by siRNA, Lipofectamine complexed with siRNA (siRNA/Lipo), siRNA complex with PEI (siRNA/PEI), RNAi-microsponge, and RNAi-microsponge condensed by PEI (RNAi-MS/PEI). The values outside parentheses indicate the concentration of siRNA and siRNA for siRNA/Lipo and siRNA/PEI. The values within parentheses indicate the concentration of RNAi-microsponge and RNAi-microsponge for RNAi-MS/PEI. The same amount of siRNA is theoretically produced from RNAi-microsponges at the concentration in parentheses. c, In vivo knockdown of firefly luciferase by RNAi-MS/PEI. Optical images of tumours after intratumoral injection of RNAi-MS/PEI into the left tumor of mouse and PEI solution only as a control into the right tumor of same mouse.
Figure 14:
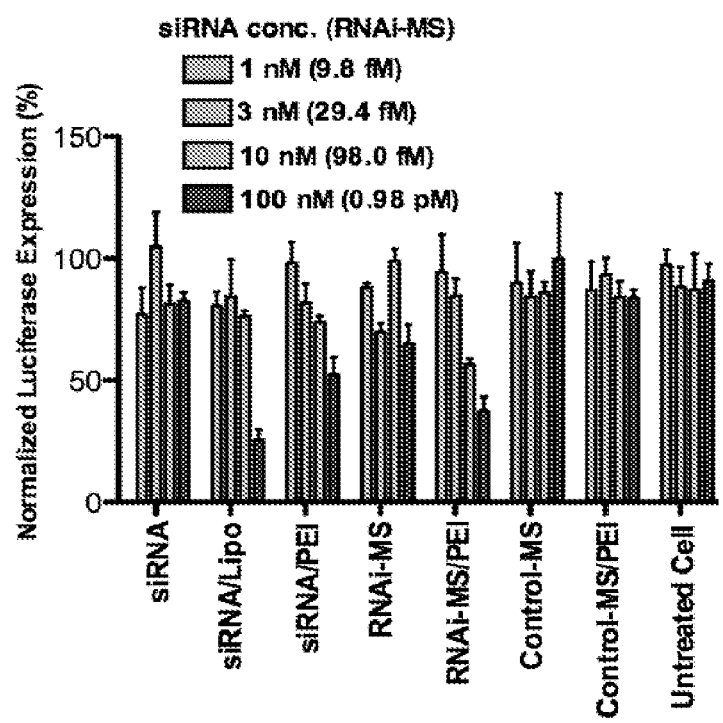
FIG. 14. In vitro knockdown of luciferase by naked siRNA, siRNA/Lipo [siRNA/Lipofectamine (commercially available gene delivery reagent) complexes], siRNA/PEI, RNAi-MS, RNAi-MS/PEI, control-MS (RNA microsponge without meaningful sequence), control-MS/PEI, and untreated cell. The results show that any significant decrease of luciferase expression is not observed by control-MS and control-MS/PEI, supporting that there is no non-specific gene regulation in our experiments.
Figure 15:
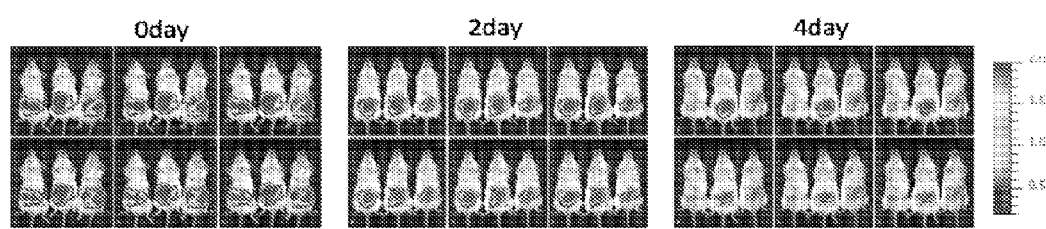
FIG. 15. In vivo knockdown of firefly luciferase by RNAi-MS/PEI. Optical images of tumours after intratumoral injection of RNAi-MS/PEI into the tumor of mouse with six different wavelength.
Figure 16:
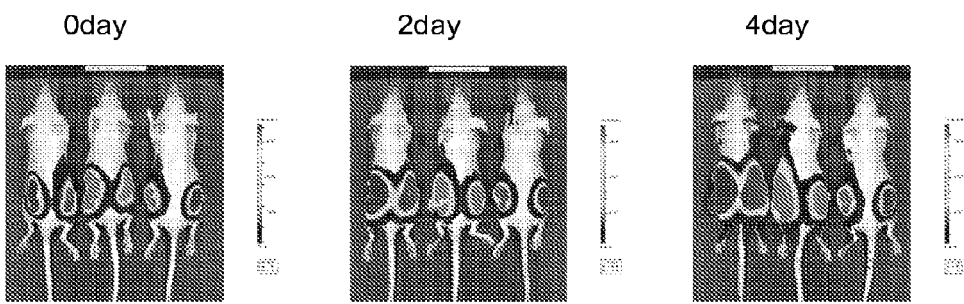
FIG. 16. In vivo knockdown of firefly luciferase by control RNA microsponge/PEI. Optical images of tumours after intratumoral injection of control RNA microsponge/PEI into the tumor of mouse. Here, control RNA microsponge dose not contain siRNA for luciferase. A significant decrease of expression is not observed.
Figure 17:
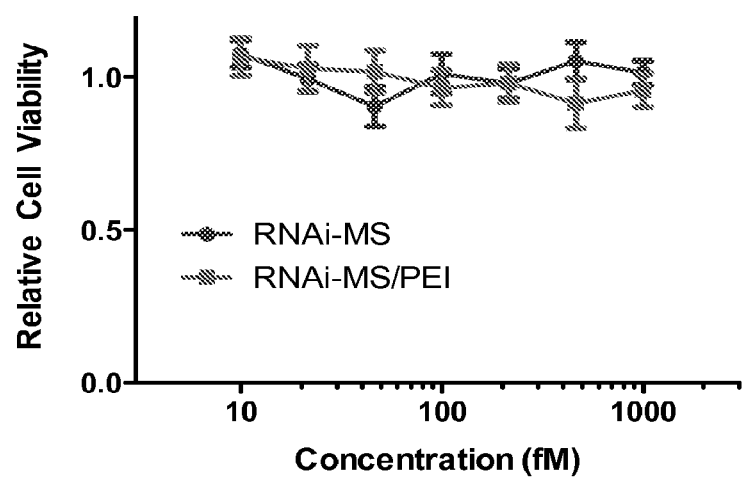
FIG. 17. Cell viability assay of RNAi-microsponges.

To confirm the cellular transfection of RNA particle, red fluorescence labeled RNAi-microsponge/PEI was incubated with T22 cells. RNAi-microsponge/PEI particles exhibited significant cellular uptake by the cancer cell line, compared with the uncondensed RNAi-microsponge (FIG. 5a). Since the RNAi-microsponge was designed to generate siRNA for silencing of firefly luciferase expression, the drug efficacy was determined by measuring the fluorescence intensity of cell lysate after transfection (FIG. 5b and FIG. 14). As expected, naked siRNA did not show any significant gene silencing up to 100 nM siRNA, whereas RNAi-microsponge showed slightly reduced gene expression at 980.0 fM. PEI layered RNAi-microsponge efficiently inhibited the firefly luciferase expression down to 42.4% at the concentration of 980 fM. The RNAi-MS/PEI delivery system shows better silencing efficiency in comparison to siRNA/PEI. The level of gene knockdown was also evaluated with in vivo optical images of firefly luciferase-expressing tumors after intratumoral injection of RNAi-microsponge/PEI (FIG. 5c and FIG. 15). As can be seen in FIG. 5c, after 4 days the level of firefly luciferase expression in the tumor was significantly reduced for the PEI layered RNAi-microsponge; however, there is no significant decrease in firefly luciferase expression with a control RNA-microsponge/PEI that does not knock down luciferase (see FIG. 16). Note that extremely low numbers (2.1 fmoles) of RNAi-microsponge/PEI particles were used to achieve significant gene silencing efficiency—roughly 3 orders of magnitude less carrier was required to achieve the same degree of gene silencing as a conventional particle based vehicle[6]. Compared to other strategies, siRNA delivery using our RNAi-microsponges provides synergistic effects for loading efficiency, drug efficacy, and low cytotoxicity (FIGS. 5b and 5c and FIG. 17).

We demonstrated that a new class of siRNA carrier, the RNAi-microsponge, which introduces a new self-assembled structure that provides a route for the effective delivery of siRNA. The RNAi microsponge presents a means of rapidly generating large amounts of siRNA in a form that assembles directly into a drug carrier that can be used for direct transfection simply by coating with a positively charged polyion. Given the high cost of therapeutic siRNA and the need for high levels of efficiency, this approach could lead to much more directly accessible routes to therapies involving siRNA. The siRNA, which is highly prone to degradation during delivery, is protected within the microsponge in the crystalline form of polymeric RNAi. We can significantly reduce the difficulties of achieving high loading efficiency for siRNA using this approach. The microsponges are able to deliver the same transfection efficiency with a three order of magnitude lower concentration of siRNA particles when compared to typical commercially available nanoparticle-based delivery. Furthermore, the ease of modification of the RNA polymer composition enables the introduction of multiple RNA species for combination therapies. The RNAi microsponge presents a novel new materials system in general due to its unique morphology and nanoscale structure within the polymer particle, and provides a promising self-assembling material that spontaneously generates a dense siRNA carrier for broad clinical applications of RNAi delivery using the intrinsic biology of the cell.

Example 2

In this Example, particles includes nucleic acid molecules comprising multiple sequences are demonstrated.

Figure 19:
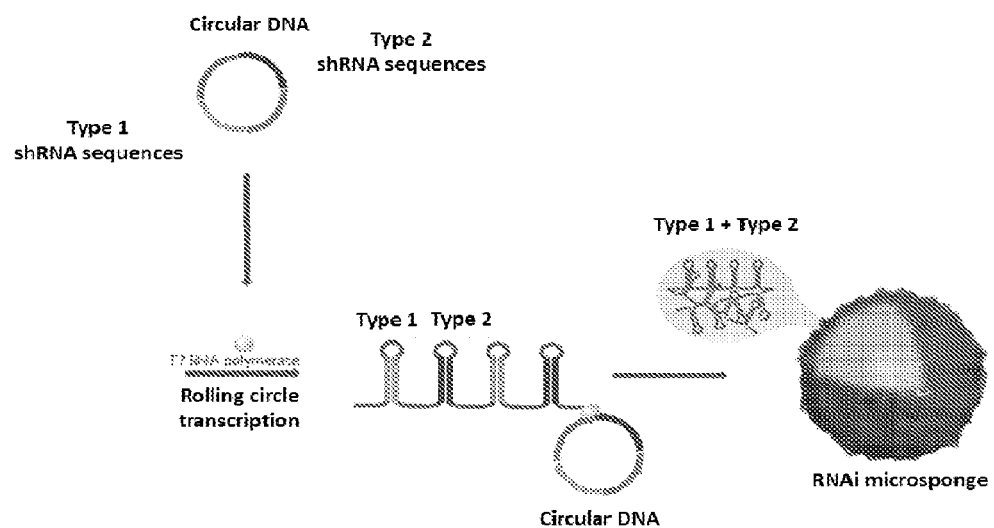
FIG. 19. Schematic illustration of multiple components RNAi microsponges in accordance with certain embodiments of the present invention.
Figure 19:
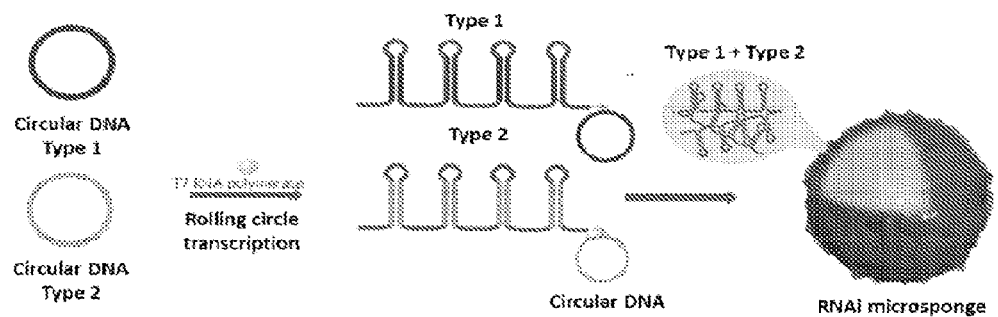

To generate the RNAi combination system, we can incorporate RNAi combinations by assembling multiple siRNA and/or microRNA (miR) within a single RNAi microsponge. To achieve this goal, multiple RNA species can be designed within a single circular DNA template. Then self-assembled RNAi microsponge can be synthesized during RCT reaction by producing multiple components from a single circular DNA template (Engineering Strategy 1 in FIG. 19). Another strategy is that we can design each type of siRNA sequences in a single circular DNA template and mix all types of circular DNA together during RCT reaction (Engineering Strategy 2 in FIG. 19). Specific composition of multiple RNAi reagents can be incorporated as components of circular DNA to generate the RNAi combination system. The numbers and types of multiple components in a single RNAi microsponge are unlimited. Possible candidates for RNAi combination systems are siRNA, shRNA, miRNA, and Ribozyme. Note that molar ratios between siRNA sequences can be varied depending on their efficacy of knockdown. A variety of parameters can be considered in the sequence design and for efficient knockdown such as RNA geometry (secondary and tertiary structures), molar ratios of multiple siRNA sequences, additional spacers between multiple siRNAs in a single transcript and destabilizing G:U wobble pairs to improve transcription efficiency.

Figure 20:
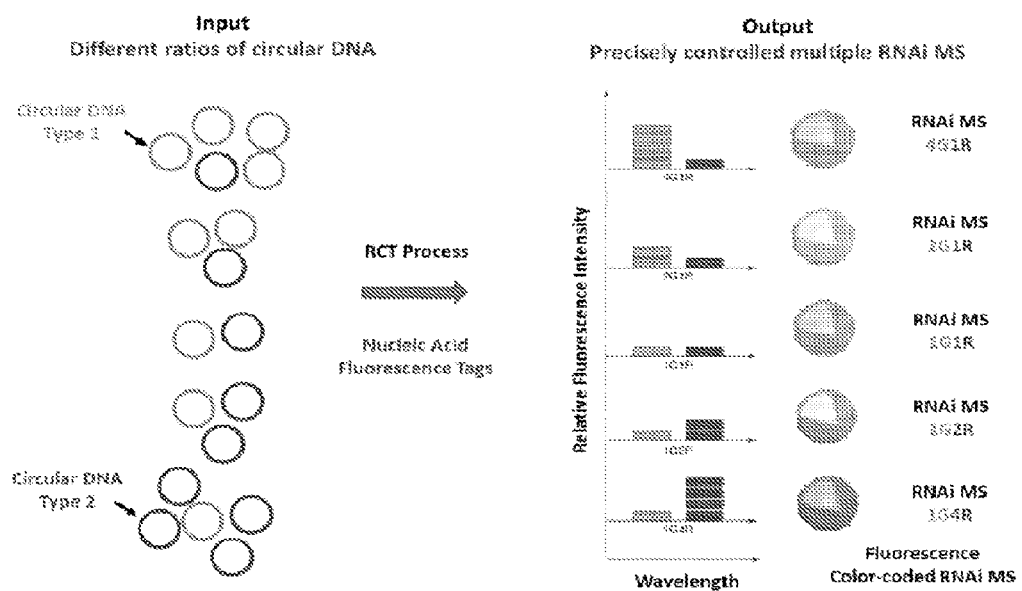
FIG. 20. Characterization of multiple components RNAi microsponges.
Figure 20:
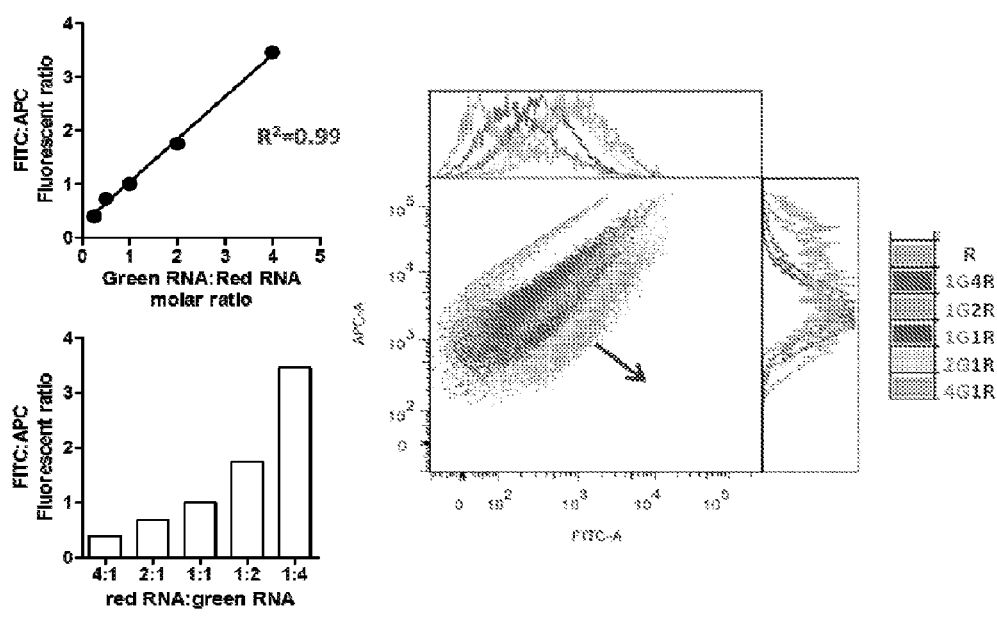

FIG. 20 shows the existence of multiple components within a single RNAi microsponge structure was confirmed by flow cytometry analysis. Various RNAi microsponges were constructed based on the molar ratios differences between two siRNA sequences by varying the molar ratio of DNA templates. Then two molecular recognition probes, fluorophores tags both green and red, were attached to each RNAi microsponge. The RNAi microsponges 4G1R, 2G1R, 1G1R, 1G2R and 1G4R were decoded based on the ratio of fluorescence intensity. FITC indicates the green channel and APC indicates the red channel. The intensity ratio $I_R/I_G$, where $I_R$ and $I_G$ were fluorescence intensities of green and red dye from both dyes-tagged RNAi microsponges respectively, was changed between the ratios of two different siRNA molecules (Figure). This result indicates that the internal structure of RNAi mircosponges consists of two siRNA components.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

We claim:

1. A particle, comprising:
a core, comprising one or more self-assembled nucleic acid molecules in a crystalline structure comprising a lamellar sheet, wherein addition of a film coating to the particle converts the core from a first configuration to a second configuration, wherein the first configuration has a first greatest dimension that is greater than 2 μm and; the second configuration has a second greatest dimension that is less than 500 nm.

2. The particle of claim 1, wherein the core contains a single nucleic acid molecule.

3. The particle of claim 1, wherein the core comprises a plurality of nucleic acid molecules.

4. The particle of claim 3, wherein the nucleic acid molecules have different nucleic acid sequences.

5. The particle of claim 3, wherein all nucleic acid molecules within the core have substantially the same nucleic acid sequence.

6. The particle of claim 3, wherein the nucleic acid molecules within the core have sequences that share at least one common sequence element.

7. The particle of claim 1, wherein at least one nucleic acid molecule within the core has a nucleotide sequence that comprises multiple copies of at least a first sequence element.

8. The particle of claim 1, wherein at least one nucleic acid molecule within the core has a nucleotide sequence that comprises multiple copies of each of at least a first and a second sequence element.

9. The particle of claim 8, wherein the at least one nucleic acid molecule has a nucleotide sequence that comprises alternating copies of the first and second sequence elements.

10. The particle of claim 8, wherein the at least one nucleic acid molecule has a nucleotide sequence that comprises multiple copies of each of three or more sequence elements.

11. The particle of claim 1, wherein at least one nucleic acid molecule has a nucleotide sequence that includes one or more sequence elements found in a natural source.

12. The particle of claim 11, wherein the at least one nucleic acid molecule has a nucleotide sequence that includes a first sequence element that is found in a first natural source and a second sequence element that is found in a second natural source.

13. The particle of claim 12, wherein the first and second natural sources are the same.

14. The particle of claim 12, wherein the first and second natural sources are different.

15. The particle of claim 1, wherein at least one nucleic acid molecule in the core has a nucleotide sequence that represents an assemblage of sequence elements found in one or more source nucleic acid molecules.

16. The particle of claim 15, wherein the at least one nucleic acid molecule has a nucleotide sequence that represents an assemblage of at least two different sequence elements found in two different source nucleic acid molecules.

17. The particle of claim 1, wherein at least a portion of the nucleic acid molecules within a core is cleavable.

18. The particle of claim 1, wherein the nucleic acid molecules within a core comprise single-stranded, double-stranded, triple-stranded nucleic acids or combination thereof.

19. The particle of claim 1, wherein the nucleic acid molecules within a core are arranged in a crystalline structure comprising lamellar sheets.

20. The particle of claim 1, wherein the nucleic acid molecules within a core comprise a stem-loop or linear structure.

21. The particle of claim 1, wherein the core comprises about $1\times10^3$ to $1\times10^8$ copies of a sequence element.

22. The particle of claim 1, wherein the core comprises at least $1\times10^6$ copies of a sequence element.

23. The particle of claim 1, wherein the nucleic acid molecules have a molecular weight of at least about $1\times10^{10}$ g/mol, about $1\times10^9$ g/mol, about $1\times10^8$ g/mol, about $1\times10^7$ g/mol, about $1\times10^6$ g/mol, or about $1\times10^5$ g/mol.

24. The particle of claim 1, wherein the core has a negative or positive surface charge.

25. The particle of claim 1, further comprising one or more agents for delivery within the core.

26. The particle of claim 25, wherein the agent is a chemotherapeutic agent selected from the group consisting of doxorubicin, carboplatin, cisplatin, cyclophosphamide, docetaxel, erlotinib, etoposide, fluorouracil, gemcitabine, imatinib mesylate, irinotecan, methotrexate, paclitaxel, sorafinib, sunitinib, topotecan, vincristine, and vinblastine.

27. The particle of claim 1, wherein the second greatest dimension of the core is less than 500 nm, less than 200 nm, less than 100 nm, less than 50 nm, less than 20 nm or less than 10 nm.

28. The particle of claim 1, further comprising a film coated on the core, and wherein the core is in the second configuration.

29. The particle of claim 28, wherein the film comprises at least one material selected from the group consisting of an organic material and an inorganic material.

30. The particle of claim 28, wherein the film comprises a polymer.

31. The particle of claim 30, wherein the film comprises a lipid.

32. The particle of claim 28, wherein the film comprises at least one polyelectrolyte layer.

33. The particle of claim 32, wherein the polyelectrolyte layer is degradable or non-degradable.

34. The particle of claim 32, wherein the polyelectrolyte layer is or comprises a polycation or polyanion.

35. The particle of claim 34, wherein the polycation is one or more member of the group consisting of polyethylenimine, poly(L-lysine) (PLL), and poly(lactic acid) (PLA).

36. The particle of claim 28, wherein the film comprises a layer-by-layer (LBL) film.

37. The particle of claim 36, wherein the LBL film comprises multiple polyelectrolyte layers.

38. The particle of claim 37, wherein the LBL film comprises multiple polyelectrolyte layers of alternating charges.

39. The particle of claim 28, wherein the film further comprises one or more agents.

40. The particle of claim 28, wherein the particle has a surface charge.

41. A method for forming the particle of claim 1 comprising: assembling one or more nucleic acid molecules into a core with a crystalline structure comprising lamellar sheets.

42. A method for forming the particle of claim 1 comprising: assembling one or more nucleic acid molecules into a core, wherein the core has a first greatest dimension greater than 2 pm, and coating the core with a film, wherein the coated core has a second greatest dimension less than 500 nm.

43. The method of claim 42, further comprising forming the nucleic acid molecules via rolling circle amplification (RCA), rolling circle transcription (RCT) or both.

44. The method of claim 43, wherein the step of forming comprises using a circular nucleic acid template.

45. The method of claim 44, wherein the step of forming comprises hybridizing the circular nucleic acid template with a primer.

46. The method of claim 45, wherein the primer is complementary to a portion of the circular nucleic acid template.

47. The method of claim 44, wherein the step of forming further comprises amplifying the circular nucleic acid template using an enzyme.

48. The method of claim 47, wherein the enzyme is Φ29 DNA polymerase, T7 polymerase or both.

49. The method of claim 42, wherein the step of coating comprises mixing the core in a coating solution.

50. The method of claim 49, wherein the coating solution comprises polyethylenimine.

51. The method of claim 42, wherein the step of coating further comprises sequentially assembling additional layers.

* * * * *